United States Patent
Beckman et al.

(10) Patent No.: US 7,470,237 B2
(45) Date of Patent: Dec. 30, 2008

(54) BIOPSY INSTRUMENT WITH IMPROVED NEEDLE PENETRATION

(75) Inventors: Andrew T. Beckman, Cincinnati, OH (US); Thomas E. Albrecht, Cincinnati, OH (US); Lee Reichel, Springboro, OH (US); Gwendolyn Ruth Perez, Cincinnati, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 152 days.

(21) Appl. No.: 11/035,873

(22) Filed: Jan. 10, 2005

(65) Prior Publication Data

US 2006/0155210 A1    Jul. 13, 2006

(51) Int. Cl.
   *A61B 10/00* (2006.01)
   *A61B 17/32* (2006.01)
   *A61B 17/14* (2006.01)
   *A61B 17/34* (2006.01)
   *A61B 17/20* (2006.01)

(52) U.S. Cl. .............. 600/564; 600/562; 600/567; 600/568; 606/167; 606/168; 606/169; 606/170; 606/171; 606/172; 606/180; 606/184; 606/185; 604/22

(58) Field of Classification Search .............. 600/562, 600/564, 567, 568; 606/167, 168, 169, 170, 606/171, 172, 180, 184, 185; 604/22
See application file for complete search history.

(56) References Cited

U.S. PATENT DOCUMENTS

| | | | |
|---|---|---|---|
| 5,526,822 A | 6/1996 | Burbank et al. | |
| 5,538,010 A * | 7/1996 | Darr et al. | 600/567 |
| 5,649,547 A | 7/1997 | Ritchart et al. | |
| 5,769,086 A | 6/1998 | Ritchart et al. | |
| 5,775,333 A | 7/1998 | Burbank et al. | |
| 5,928,164 A | 7/1999 | Burbank et al. | |
| 5,951,489 A * | 9/1999 | Bauer | 600/567 |
| 5,964,716 A | 10/1999 | Gregoire et al. | |
| 5,980,469 A | 11/1999 | Burbank et al. | |
| 6,007,497 A | 12/1999 | Huitema | |
| 6,017,316 A | 1/2000 | Ritchart et al. | |
| 6,086,544 A | 7/2000 | Hibner et al. | |
| 6,120,462 A | 9/2000 | Hibner et al. | |
| 6,228,005 B1 | 5/2001 | Gray | |
| 6,231,522 B1 | 5/2001 | Voegele et al. | |
| 6,273,862 B1 | 8/2001 | Privitera et al. | |
| 2003/0199753 A1 | 10/2003 | Hibner et al. | |
| 2004/0158172 A1 | 8/2004 | Hancock | |

OTHER PUBLICATIONS

EnCor™ MRI Specifications and Breast Biopsy System, SenoRx, 2005, pp. 102.
EPO Search Report, Application No. 06250083.0, May 27, 2006, pp. 1-4.

\* cited by examiner

*Primary Examiner*—Max Hindenburg
*Assistant Examiner*—Jeffrey G Hoekstra

(57) ABSTRACT

The present invention provides a biopsy instrument with improved needle penetration for piercing dense tissue. The device may comprise a needle slidably retained in a housing. The device may further comprise an actuation member that may be adapted to communicate longitudinal motion to the needle in a first direction. The device may further include a propulsion element that provides the needle with return motion in a second direction. The device may be fired multiple times to create repeating reciprocal motion. In one version, the device may reciprocate several times as a result of a single engagement of the actuation member.

20 Claims, 26 Drawing Sheets

BIOPSY INSTRUMENT WITH IMPROVED NEEDLE PENETRATION

FIELD OF THE INVENTION

The present invention relates to handheld biopsy instruments and, more particularly, to generating a pulsating or reciprocating motion in the needle of a biopsy instrument in order to provide improved tissue and lesion penetration by the instrument.

BACKGROUND OF THE INVENTION

When a suspicious tissue mass is discovered in a patient's breast through examination, ultrasound, MRI, X-ray imaging or the like, it is often necessary to perform a biopsy procedure to remove one or more samples of that tissue in order to determine whether the mass contains cancerous cells. A biopsy may be performed using an open or percutaneous method.

An open biopsy is performed by making a large incision in the breast and removing either the entire mass, called an excisional biopsy, or a substantial portion of it, known as an incisional biopsy. An open biopsy is a surgical procedure that is usually done as an outpatient procedure in a hospital or a surgical center, involving both high cost and a high level of trauma to the patient. Open biopsy carries a relatively higher risk of infection and bleeding than does percutaneous biopsy, and the disfigurement that sometimes results from an open biopsy may make it difficult to read future mammograms. Further, the aesthetic considerations of the patient make open biopsy even less appealing due to the risk of disfigurement. Given that a high percentage of biopsies show that the suspicious tissue mass is not cancerous, the downsides of the open biopsy procedure render this method inappropriate in many cases.

Percutaneous biopsy, to the contrary, is much less invasive than open biopsy. Percutaneous biopsy may be performed using fine needle aspiration (FNA) or core needle biopsy. In FNA, a very thin needle is used to withdraw fluid and cells from the suspicious tissue mass. This method has the advantage that it is very low-pain, so low-pain that local anesthetic is not always used because the application of it may be more painful than the FNA itself. However, a shortcoming of FNA is that only a small number of cells is obtained through the procedure, rendering it relatively less useful in analyzing the suspicious tissue and making an assessment of the progression of the cancer if the sample is found to be malignant.

Core needle biopsy provides for removal of a small tissue sample that allows a pathological assessment of the tissue, including an assessment of the progression of any cancerous cells that are found. The following patent documents disclose various biopsy devices and are incorporated herein by reference in their entirety: U.S. Pat. No. 6,273,862 issued Aug. 14, 2001; U.S. Pat. No. 6,231,522 issued May 15, 2001; U.S. Pat. No. 6,228,055 issued May 8, 2001; U.S. Pat. No. 6,120,462 issued Sep. 19, 2000; U.S. Pat. No. 6,086,544 issued Jul. 11, 2000; U.S. Pat. No. 6,077,230 issued Jun. 20, 2000; U.S. Pat. No. 6,017,316 issued Jan. 25, 2000; U.S. Pat. No. 6,007,497 issued Dec. 28, 1999; U.S. Pat. No. 5,980,469 issued Nov. 9, 1999; U.S. Pat. No. 5,964,716 issued Oct. 12, 1999; U.S. Pat. No. 5,928,164 issued Jul. 27, 1999; U.S. Pat. No. 5,775,333 issued Jul. 7, 1998; U.S. Pat. No. 5,769,086 issued Jun. 23, 1998; U.S. Pat. No. 5,649,547 issued Jul. 22, 1997; U.S. Pat. No. 5,526,822 issued Jun. 18, 1996; and US Patent Application 2003/0199753 published Oct. 23, 2003 to Hibner et al.

It is known in the art for core needle biopsy devices to include a firing mechanism which allows the needle and a cutter to thrust forward in order to obtain a tissue sample.

Frequently, a surgeon may encounter an area of dense tissue that is more difficult to penetrate than the surrounding tissue during core needle biopsy. In particular, the lesion or tissue mass being targeted in the biopsy procedure may be difficult to penetrate, requiring the physician to push the biopsy needle with considerable force and/or speed in an attempt to penetrate the lesion and collect a sample.

When encountering such an area of dense tissue, it is common for surgeons using the type of firing core needle biopsy device described above to fire the device in order to penetrate the lesion and obtain a sample. However, due to the length of the firing stroke of such devices, which can be as long as 0.75 inches, it is nearly impossible for the surgeon to control the travel of the needle after firing.

The long needle stroke may cause uncertainty as to the needle tip location post fire. This may cause the surgeon to obtain a sample from the wrong area. In addition to missing the targeted tissue, long firing strokes may cause the needle to puncture the chest wall or pierce the skin, particularly when the targeted area is near the patient's chest wall. Even if the skin is not pierced, the long travel of the needle, along with the likelihood that the needle will be pushed off course by the force of the firing stroke, may lead to needlessly increased trauma for the patient.

Based on surgeons' use of the long sampling stroke feature of current devices to aid in penetrating tissue lesions, it is clear that the medical community sees the benefit of firing assistance when inserting a probe to the desired location. However, the current devices incorporating a sampling stroke are not intended for, nor properly designed to, aid in penetration of dense tissue.

Consequently, a significant need exists for a core needle biopsy device that aids the surgeon in penetrating areas of dense tissue without utilizing an excessively long firing stroke that may throw the biopsy device off course, causing the patient unnecessary trauma and possibly causing the surgeon to obtain a sample from outside the targeted area. A need also exists for a device capable of a firing stroke to assist in penetrating dense tissue to properly locate the needle before advancing the cutter through the needle.

BRIEF SUMMARY OF THE INVENTION

The present invention overcomes the above-noted and other deficiencies of the prior art by providing an improved biopsy device that enables the surgeon to apply a reciprocating motion to a needle. By engaging a firing mechanism, the surgeon may impart a penetrating force to the needle that assists in piercing especially dense tissue when inserting the biopsy device through breast tissue.

In one version, the device may provide a housing and a needle having a proximal portion and a distal portion, the proximal portion being slidably retained within the housing. The device may further comprise a firing mechanism adapted to releasably engage the needle. The firing mechanism may be adapted to move the needle longitudinally from a default position to a release position. The needle may be further adapted to disengage the firing mechanism once it reaches the release position. The device may further comprise a propulsion element in communication with the needle such that it may be adapted to propel the needle distally when the needle disengages the actuating member. This version advantageously allows the surgeon to impart a back-and-forth longitudinal motion to the needle in order to penetrate dense tissue.

In another aspect, the biopsy device may comprise a housing and a needle comprising a lumen, a proximal portion and a distal portion. The proximal portion of the needle may be slidably retained within the housing. The device may further comprise a firing mechanism adapted to releasably engage the needle. The firing mechanism may be adapted to move the needle longitudinally from a default position to a release position. The needle may be further adapted to disengage the firing mechanism once it reaches the release position. The device may further comprise a cutter adapted to be advanced within the lumen of the needle independently of the firing mechanism. Therefore, the surgeon may advance the cutter through the needle after the distal portion of the needle has been placed adjacent the tissue of interest. In this manner, the surgeon may take advantage of a firing stroke of the needle to penetrate dense tissue without advancing the cutter into the tissue prematurely.

In one aspect, the needle biopsy device may comprise a housing and a needle. A proximal portion of the needle may be retained within the housing. The device may include a firing mechanism adapted to releasably engage the needle and to move the needle longitudinally from a default position to a release position. The needle may be adapted to disengage the firing mechanism when it reaches the release position. The device may further comprise a spring adapted to return the needle to the default position when it reaches the release position. In this manner, the device may provide a reciprocal motion to the needle to allow the surgeon to accurately place the needle adjacent the sampling site.

In another version, the device may include a housing comprising an actuating member adapted to engage a lever. The lever may comprise an angled edge including one or more cutbacks. The lever may further comprise a recess subdivided by one or more partitions. The device may comprise a needle including a lever-engaging element that is adapted to engage each of the subdivisions of the recess. The lever may be adapted to receive motion from the actuating member to move from a default position to a release position, causing the needle to move to the release position as well, due to the engagement therebetween. The housing may further comprise a tripping element. When the lever is moved toward the release position, the angled surface of the lever may be adapted to ride on the tripping element, causing a distal portion of the lever to rotate away from the needle. The lever-engaging element of the needle may be adapted to disengage a first subdivision of the lever recess at the predetermined release position. The device may further comprise a compression spring that may be adapted to propel the needle longitudinally when the needle disengages the lever.

The tripping element may be adapted to encounter one of the cutbacks on the angled surface just after release of the needle from the first subdivision. The device may further include a return spring that is adapted to return the lever to a substantially horizontal position when the tripping element encounters the first cutback, causing a second subdivision of the recess to engage the lever-engaging element of the needle. As the actuating member continues toward the fully engaged position, the angled surface of the lever may continue to ride the tripping element, causing its distal portion to again rotate away from the needle, eventually causing the needle to disengage the second subdivision and travel toward the return position. In this manner, the needle may be capable of traveling from an initial release position back to a return position in a series of staccato pulses.

In an alternative aspect of the invention, the biopsy device comprises a housing that may include an actuating member that is moveable from a first, non-activated position to a second, activated position. The device may further include a needle that may comprise a proximal portion and a distal portion, wherein the proximal portion may be retained within the housing of the device. The device may also include a driving member that may be slidably connected to the housing such that it is moveable from a default position to a release position. The actuating member may be adapted to engage the driving member such that motion is communicated to the driving member from the actuating member. In this manner, when the actuating member is moved from a first, non-activated position to a second, activated position, the driving member may be moved proximally within the housing from the default position to the release position. The device may also include a spring in communication with the driving member and the housing such that when the driving member is moved from the default position to the release position, potential energy is stored within the spring. The driving member may be adapted to disengage the actuating member when it reaches a predetermined release position, which may cause the spring to convert its stored potential energy to kinetic energy and propel the driving member distally within the housing. When propelled distally by the spring, the driving member may pass through the default position and impact the proximal portion of the needle, forcing it distally from a resting position to an extended position. The housing may include a dampening element that is adapted to return the needle from the extended position to the resting position. This version has the advantage of providing distal then proximal motion to the needle, which may advantageously prevent the needle from moving distally within the device's housing under the force encountered when it is pushed through tissue even if the device is not being fired.

In yet another aspect of the invention, the biopsy device includes a housing that may comprise an actuating member that is moveable from a first, non-activated position to a second, activated position. The housing may further comprise a lead screw in rotatable engagement with the housing. The device may also include a nut that may be adapted to ride on the lead screw. The actuating member may be adapted to engage the nut so that movement of the actuating member from the first, non-activated position to the second, activated position causes the nut to translate along the length of the lead screw. The lead screw may be adapted to rotate in reaction to translation of the nut along the length of the lead screw. The device may further include a first cam that is connected with a distal end of the lead screw such that rotation of the screw also causes the first cam to rotate. The first cam may include a distal face comprising an uneven surface. The device may further include a needle having a proximal portion and a distal portion, wherein the proximal portion may be contained within the housing. The needle may further be connected to a second cam at its proximal portion. The second cam may include a proximal face comprising an uneven surface that is adapted to contact the distal face of the first cam. The needle may further be connected to a return spring that is in communication with a proximal wall of the housing.

In this version, rotation of the screw may cause the uneven surface of the distal face of the first cam to rotate against the uneven surface of the proximal face of the second cam. Depending on the point of the rotation of the first cam against the second cam, the interaction between uneven surfaces of the first and second cam, respectively, may be adapted to alternately push the second cam away from the first cam, then allow it to be pushed closer to the first cam by the biasing force provided by the return spring. As the second cam is alternately pushed distally and proximally by the first cam and return spring, respectively, the needle may also experience reciprocal motion. This version of the device is advantageous because a single movement of the actuating member from the first, non-activated position to the second, fully-activated position may allow the needle to undergo multiple reciprocations, depending on the number of rotations of the first cam against the second cam.

The present invention also extends to a method of penetrating dense tissue and obtaining a tissue comprising the steps of (i) inserting a needle biopsy device into tissue; (ii) actuating a reciprocating firing stroke of a needle to penetrate dense tissue before advancing a cutter through the needle; and (iii) advancing the cutter through the biopsy device and obtaining a sample after the device has been placed adjacent the tissue of interest. With this method, the surgeon may advantageously penetrate dense tissue by utilizing a reciprocating feature of the needle without prematurely and dangerously advancing the cutter into the tissue.

BRIEF DESCRIPTION OF THE DRAWINGS

While the specification concludes with claims particularly pointing out and distinctly claiming the present invention, it is believed the same will be better understood by reference to the following description, taken in conjunction with the accompanying drawings, in which:

DETAILED DESCRIPTION OF THE INVENTION

The present invention pertains to a core needle biopsy device and, more particularly, to reducing the necessary manual force that must be applied by a surgeon to penetrate tissue and/or lesions with the needle of a biopsy instrument. Accordingly, the present invention provides a device for reducing the required force to penetrate tissue and/or lesions during a biopsy procedure. In particular, the invention provides for one or more short, controlled impulses by a biopsy needle to assist in advancing the needle through dense or hardened tissue. The short, controlled movements enabled by the present invention provide for improved needle position control and tracking, particularly adjacent to the chest wall. In one version, the invention may allow the surgeon to actuate short impulses of the needle independently of a separate cutter, which may be advanced after the needle has been positioned adjacent the suspicious tissue. The firing mechanism allowing the surgeon to produce controlled needle impulses may be adapted such that it does not interfere with the advancement of a separate cutter element after the needle has been properly positioned.

Figure 1:
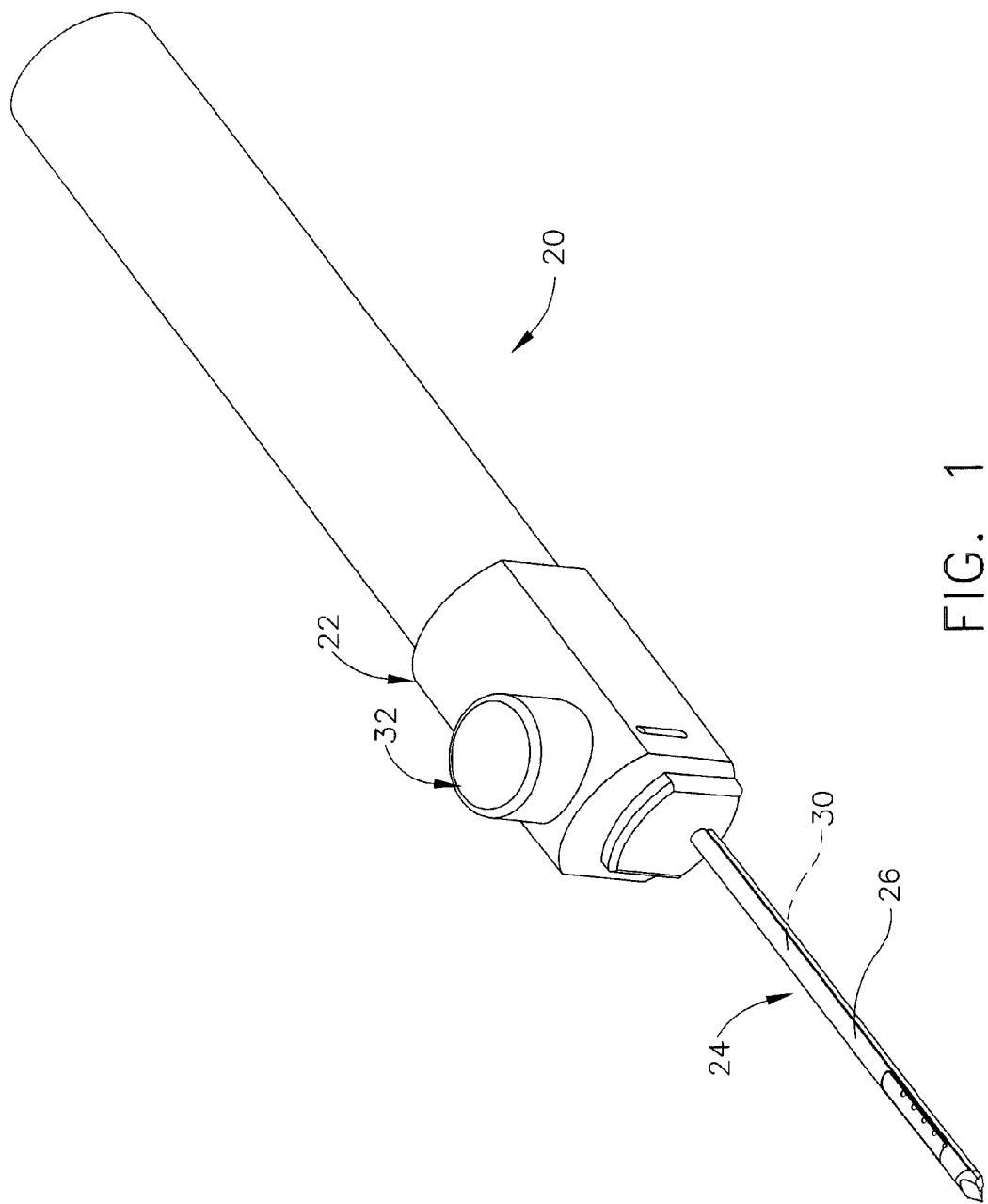
FIG. 1 is a perspective view of a representative biopsy instrument incorporating the needle driving mechanism of the present invention.

Referring now to the drawings in detail, wherein like numerals indicate the same elements throughout the views, FIG. 1 depicts a core needle biopsy instrument identified generally as numeral 20. Instrument 20 may comprise a handpiece 22 and a needle 24 supported by and extending distally from handpiece 22. In one embodiment, handpiece 22 may be ergonomically designed to enable instrument 20 to be operated with a single human hand. Needle 24 may comprise an elongated, metallic cannula 26 with a lumen 30 extending axially therethrough. The distal end of needle 24 may be sharpened to enable needle 24 to penetrate tissue. Alternatively, a separate end piece may be attached to the distal end of cannula 26. The end piece may have any number of shapes suitable for penetrating tissue. In one version, a cutter (not pictured) may be advanced through lumen 30 after needle 24 has been accurately placed adjacent tissue 38 in order to obtain a sample.

Instrument 20 may comprise a firing mechanism for imparting motion to needle 24. In one version, the firing mechanism may include an actuating member for imparting a driving force to needle 24. The actuating member may be a trigger button 32, such as that shown in FIG. 1. Alternatively, the actuating member may be any other type of button, switch, lever or knob that can be manually operated with a single human hand while simultaneously holding handpiece 22. The actuating member may be provided adjacent the distal end of handpiece 22 as shown, or anywhere else on handpiece 22 where the member may be conveniently accessed by a technician during operation of biopsy instrument 20. For instance, the actuating member may also be placed at a proximal end of handpiece 22 opposite the needle, on a lower surface of handpiece 22, on the sides of handpiece 22, or at the distal end of handpiece 22 above or below needle 24.

Figure 2:
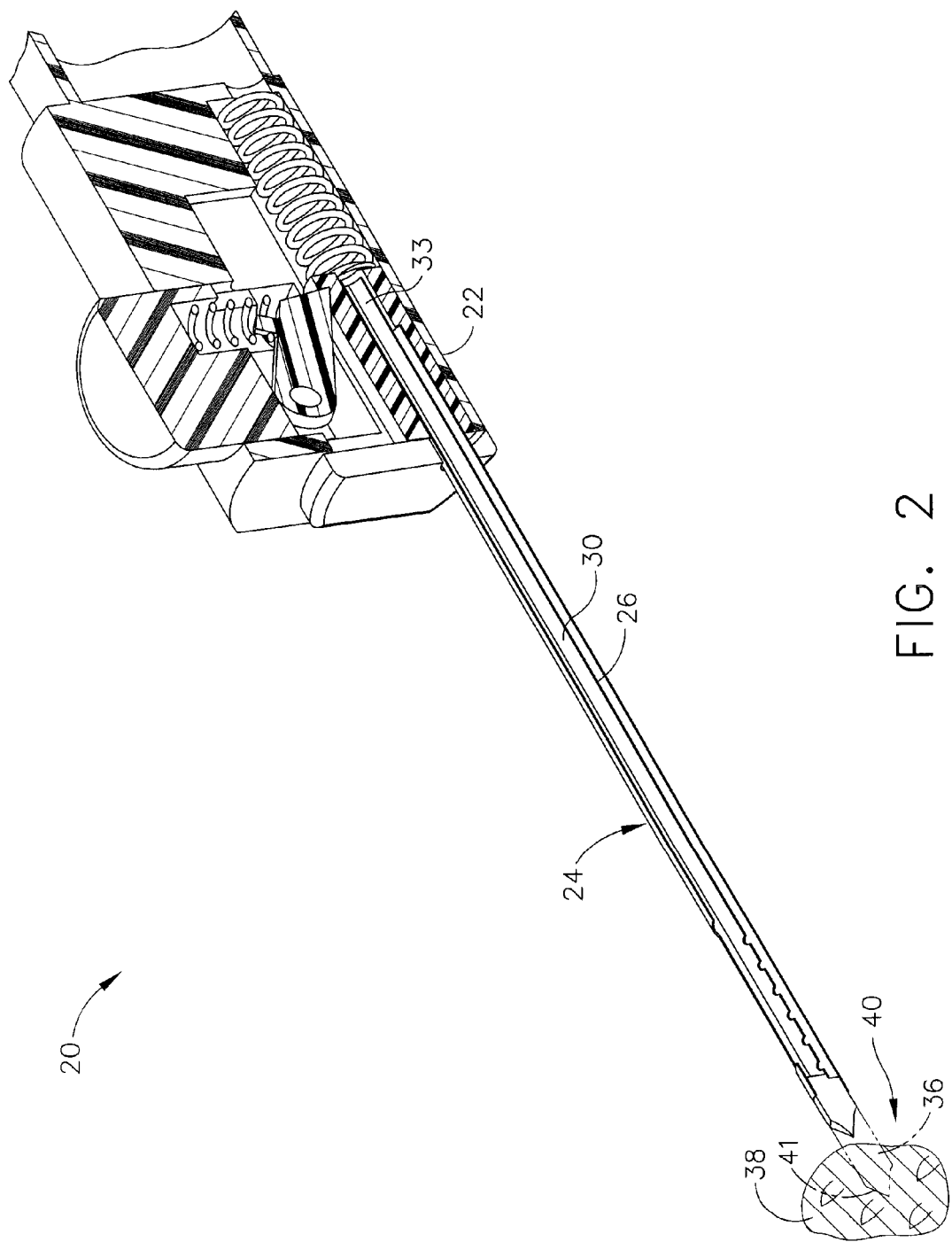
FIG. 2 is a simplified, cross-sectional view of one version of the biopsy instrument of FIG. 1, illustrating axial impulse motion imparted to the needle by a needle driving mechanism.

FIG. 2 is a diagrammatic view of the present invention illustrating the application of one or more impulse forces on needle 24. An impulse force may be imparted to a proximal portion 33 of needle 24 in order to drive the distal tip 36 of needle 24 into surrounding tissue, identified in FIG. 2 by numeral 38. In one aspect of the present invention, the impulse force may produce a short, controlled stroke of less than 0.5 inches at the needle tip. More particularly, needle travel may be less than 0.2 inches. A relatively short needle stroke may enable the physician to have greater control and certainty over the position of needle 24 within the tissue. As shown in FIG. 2, an impulse force may be imparted in the direction of the needle axis, as shown by arrow 40, to produce an axial impulse motion in needle 24, as indicated by dashed lines 41. It is also possible to impart impulse forces to needle 24, to produce an up and down motion at needle tip 36. A rotary force may also be applied in order to produce a circular penetration force at needle tip 36. Additionally, one or more directional impulse forces may be combined in order to produce a multidirectional penetration force. A single activation of the actuating member may impart a series of impulse forces to needle 24, thereby producing a repetitive, pulsating force at needle tip 36. Alternatively, the actuating member may be repetitively actuated to produce a pulsating force at needle tip 36. In the present invention, the impulse forces drive needle 24 separately from a cutter in order to improve tissue penetration prior to cutting.

FIGS. 3-6 are simplified, cross-sectional views of a biopsy instrument illustrating a firing mechanism for imparting an impulse force to needle 24. In the following discussion, the cross-sectional views of each of the versions have been simplified to show only the needle driving aspects of the biopsy instrument. In the version shown in FIG. 3, needle 24 may be driven in a backward and forward motion along the longitudinal axis of the needle. In this version, a trigger button 32 is shown as the actuating member for the mechanism, and may be moveable from a first, non-activated position to a second, activated position. In this version, trigger button 32 may be pivotally attached to a driving arm 46 by a pin 47. Arm 46 may extend from trigger button 32 to a hub 48 of needle 24. Adjacent hub 48, arm 46 may include a protrusion 50. Protrusion 50 may engage a recess 52 formed in an outer surface 53 of hub 48. Trigger button 32 may be activated by depressing the outer surface of the button 32, which may cause arm 46 to pivot towards hub 48, decreasing an angle 54 between arm 46 and hub 48. A first resilient spring 56 may be positioned between hub 48 and a fixed wall 57 within handpiece 22. As arm 46 is depressed, the engagement between protrusion 50 and recess 52 may push hub 48 proximally within handpiece 22, as indicated by arrow 58. The movement of hub 48 proximally within handpiece 22 may compress spring 56, storing potential energy therein.

Figure 3:
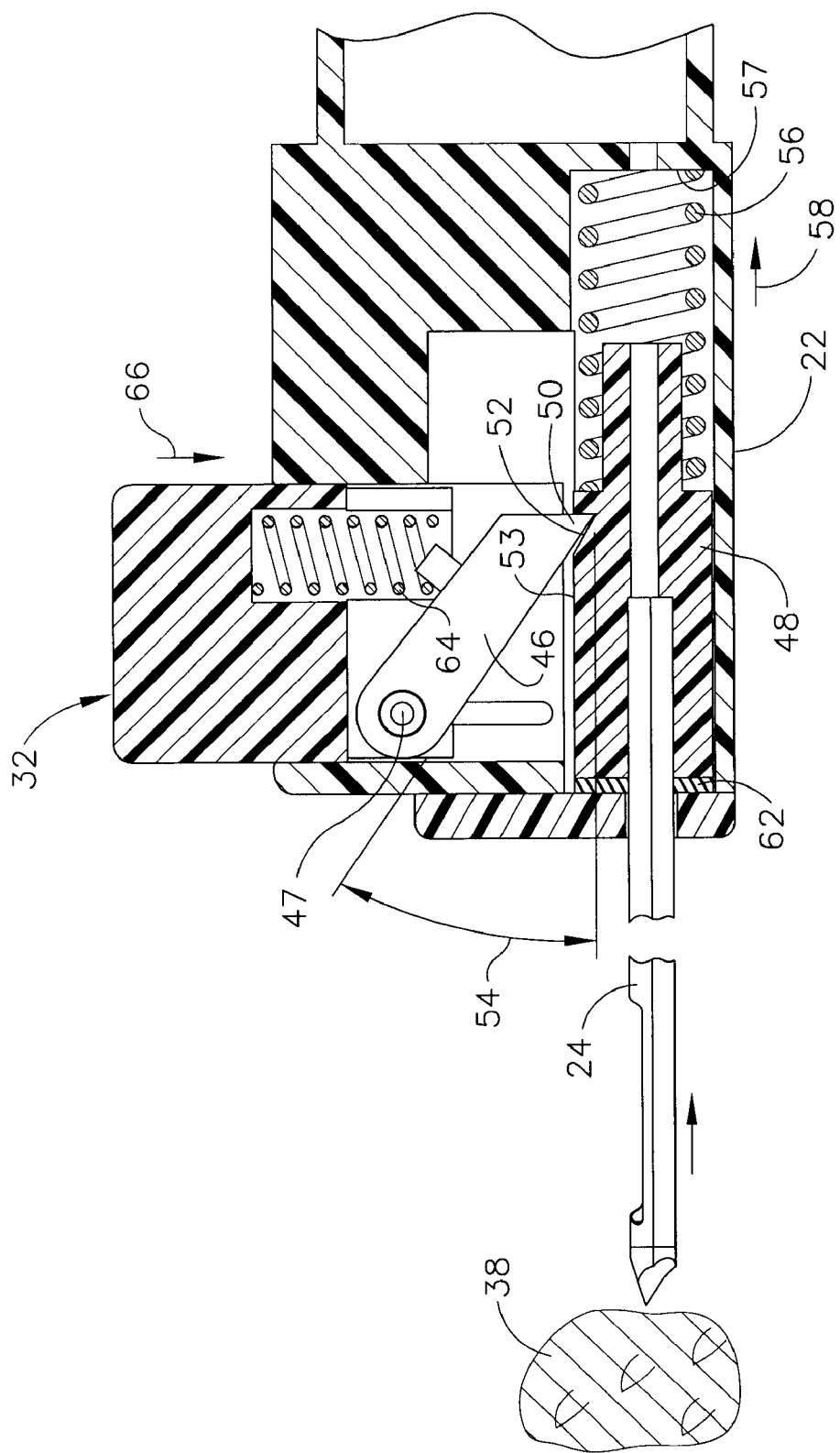
FIG. 3 is a simplified, cross-sectional view of the biopsy instrument of FIG. 1, illustrating a first version of a needle driving mechanism in which the needle is being cocked for firing.
Figure 4:
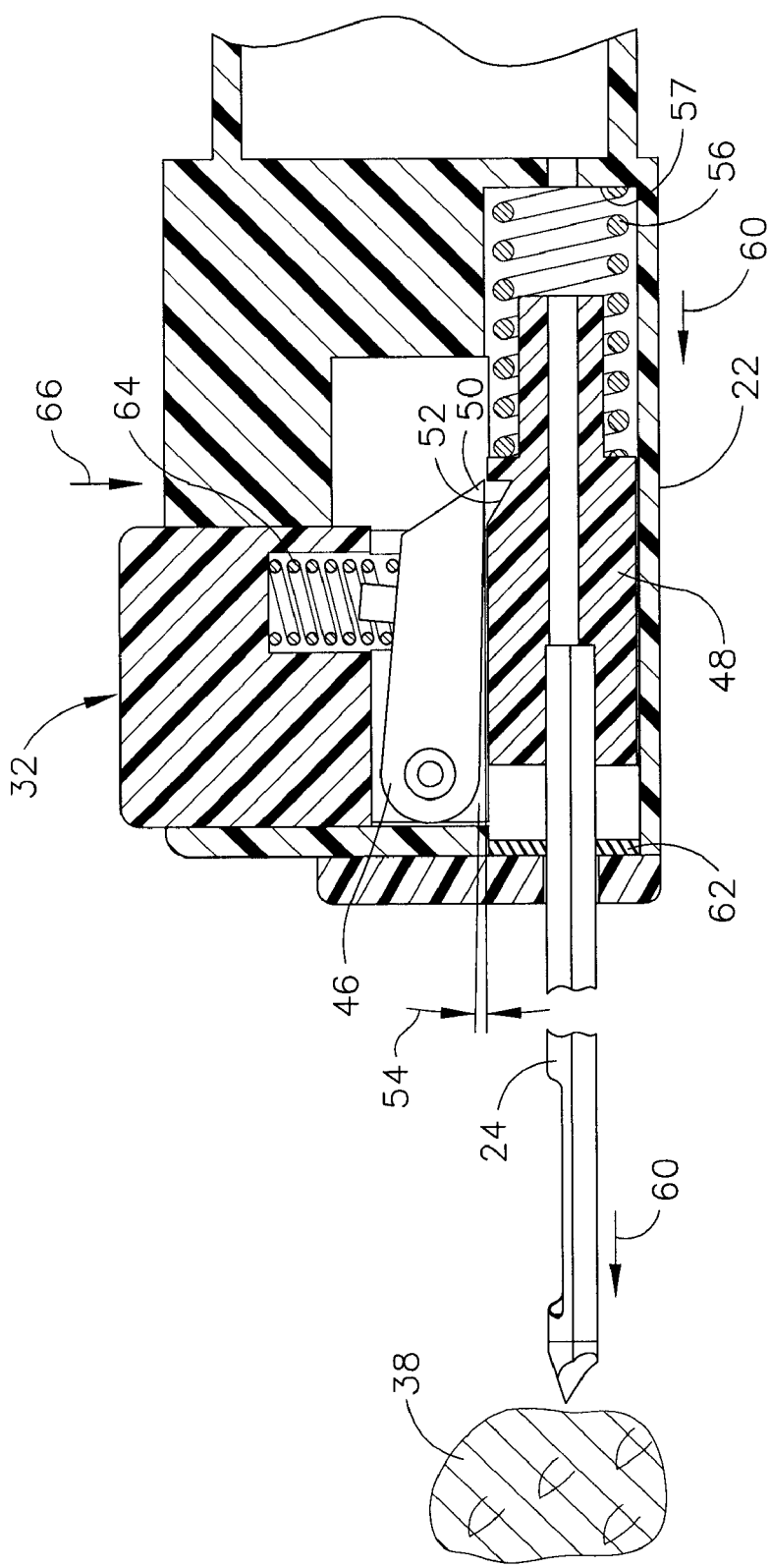
FIG. 4 is a simplified, cross-sectional view similar to FIG. 3, illustrating the needle being fired in a forward direction.
Figure 5:
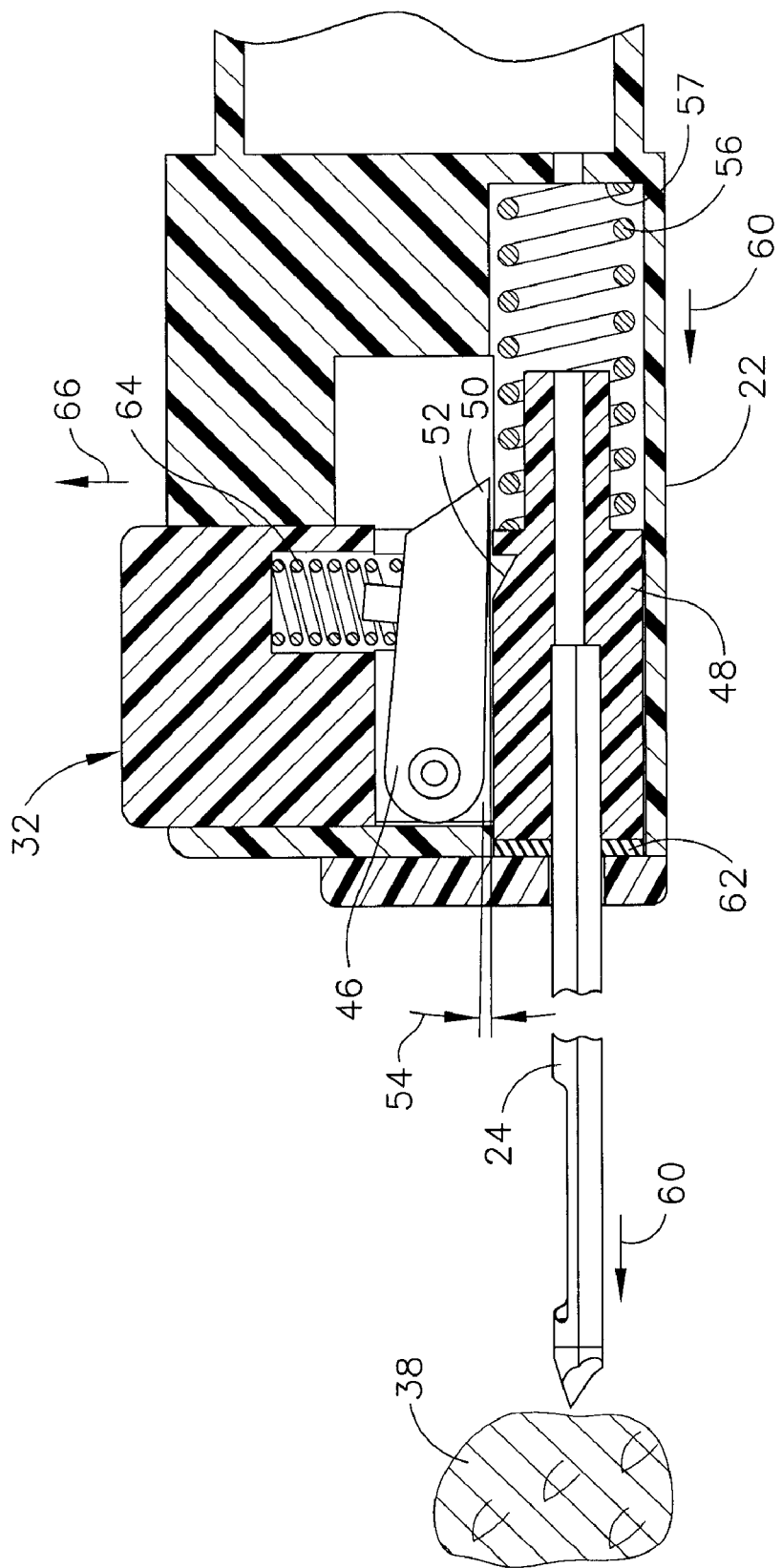
FIG. 5 is a simplified, cross-sectional view similar to FIG. 3, illustrating the dampening pad absorbing the energy released by the compression spring.
Figure 6:
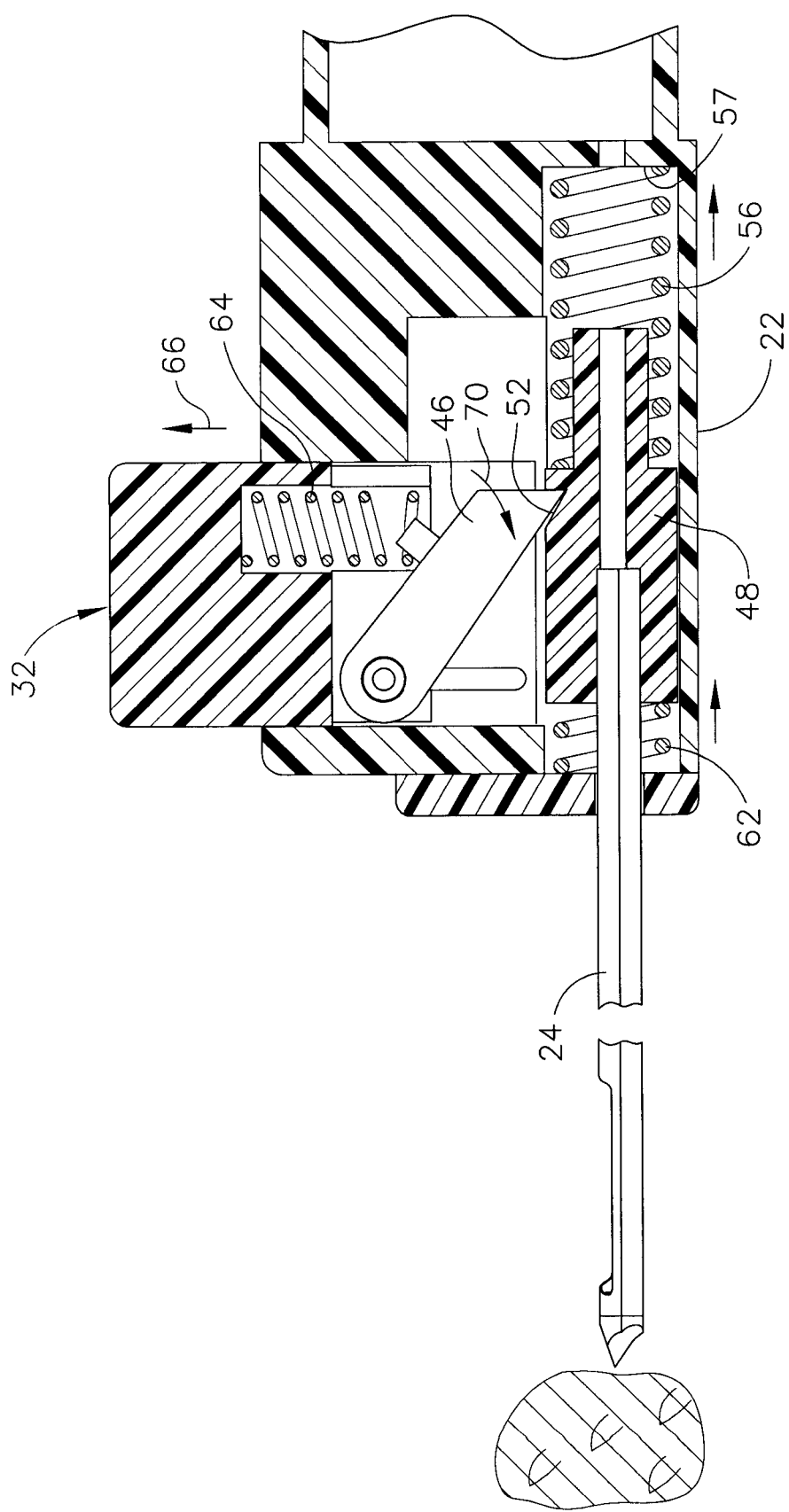
FIG. 6 is a simplified, cross-sectional view similar to FIG. 3, illustrating the driving mechanism returning to a non-activated position following firing.

Referring now to FIG. 4, as button 32 continues depressing towards the second, activated position, arm 46 may continue pivoting towards a horizontal orientation until reaching a point where protrusion 50 is adapted to disengage recess 52. As arm 46 disengages hub 48, spring 56 may be adapted to release its stored potential energy against hub 48, driving hub 48 and needle 24 distally, as indicated by arrows 60 in FIG. 4. A damping spring or pad 62 may be in communication with needle 24 distal of hub 48. As hub 48 is driven distally by first spring 56, dampening pad 62 may compress between hub 48 and a fixed portion of handpiece 22. The energy in damping pad 62 is absorbed to reduce impact sound. Instrument 20 may include a spring 64 in communication with arm 46 beneath trigger button 32. As button 32 is depressed, spring 64 may compresses between hub 48 and button 32 due to the engagement between protrusion 50 and recess 52. When arm 46 is released from hub 48, spring 64 may expand, driving hub 48 and needle 24 forward against damping pad 62, as indicated by arrow 60 in FIG. 4 and FIG. 5. Damping pad 62 may return hub 48 and needle 24 to their default position, as shown in FIG. 3. After button 32 is released by the user, it may return to the first, non-activated position, as indicated by arrow 66 in FIG. 5 and FIG. 6, pivoting arm 46 back into engagement with recess 52, as indicated by arrow 70 in FIG. 6. After returning to the non-activated position, trigger button 32 may be reactivated to impart another impulse force to needle 24. In this manner, trigger button 32 may be repetitively actuated, and needle 24 reciprocated between the distal default position and the proximal release position in order to produce an axial pulsating force in the needle. The sequential motion imparted to needle 24 in this version is a backward, forward, backward penetration force.

Figure 7:
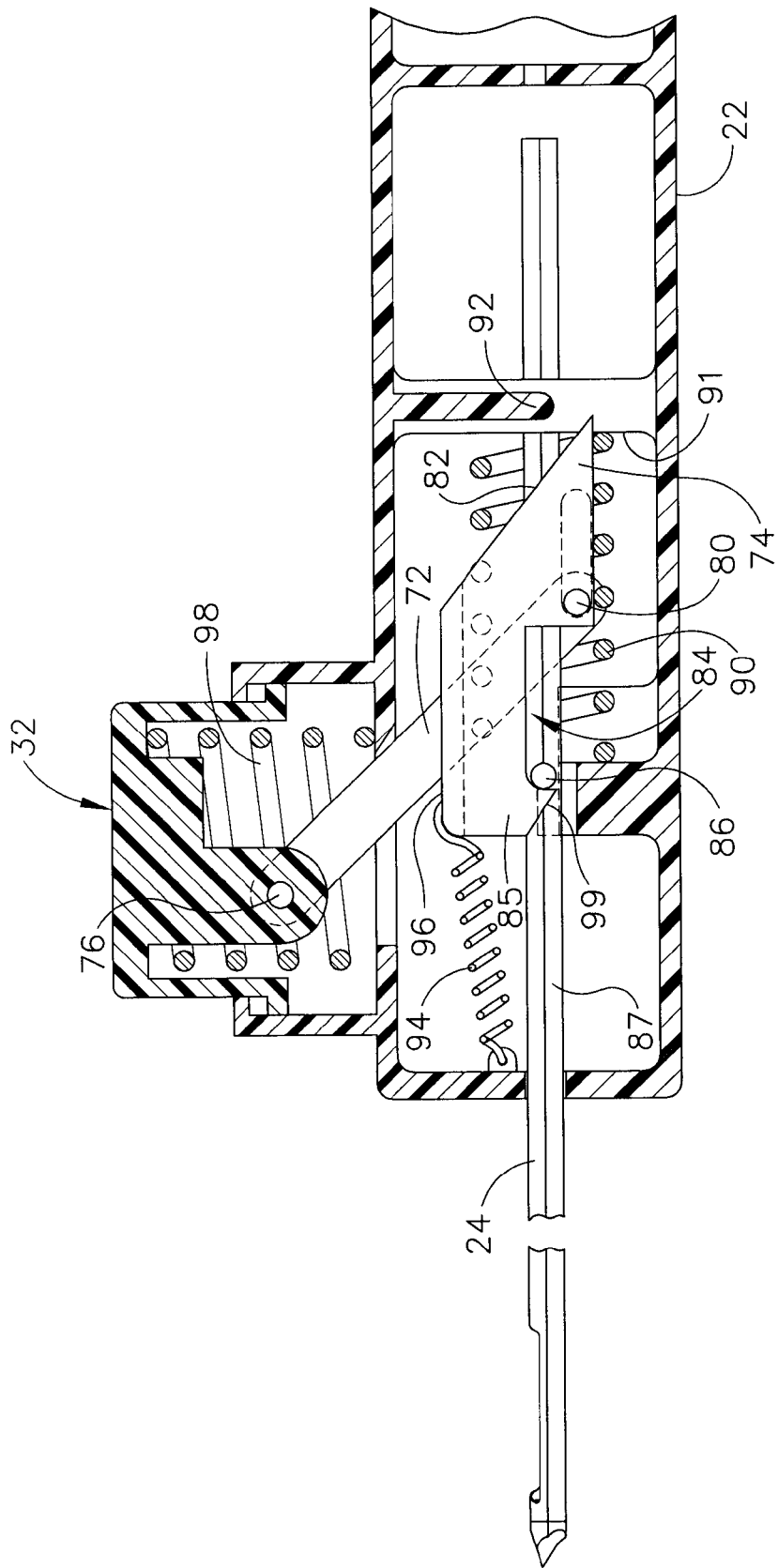
FIG. 7 is a simplified, cross-sectional view of the biopsy instrument of FIG. 1, illustrating an alternative version of a needle driving mechanism.
Figure 8:
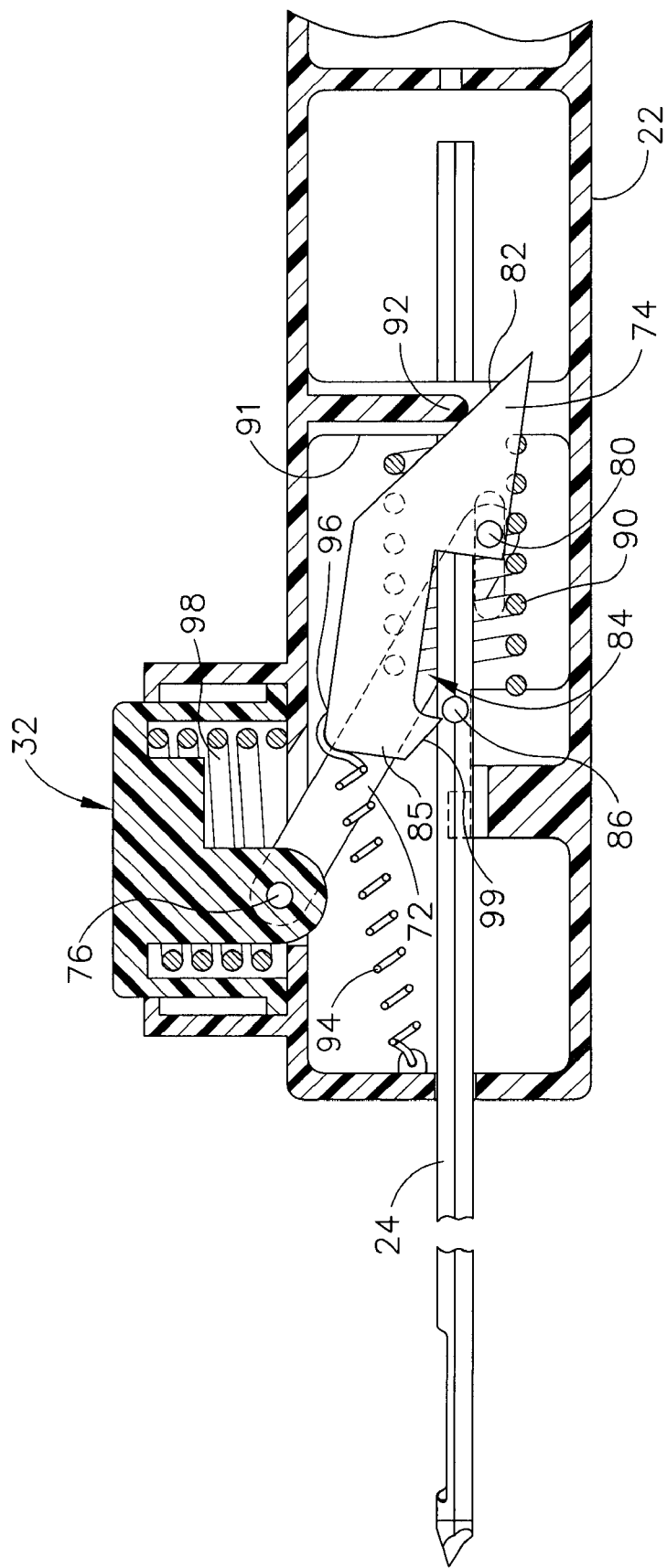
FIG. 8 is a simplified, cross-sectional view similar to FIG. 7, illustrating the needle driving mechanism in a pre-firing, activated position.

FIG. 7 illustrates an alternative mechanism for imparting an impulse force to needle 24. In the version shown in FIG. 7, the firing mechanism includes an actuating member that is again shown as a trigger button 32 that may be adapted to produce an axial impulse force in needle 24. In this version, however, a linkage 72 may connect trigger button 32 to a lever 74. Linkage 72 may be attached to trigger button 32 by a first pivot pin 76 and to lever 74 by a second pivot pin 80. As shown in FIG. 7, lever 74 may include an angled proximal end 82. A longitudinally extending recessed area 84 may also be shaped into lever 74 adjacent a distal end 85 thereof. A post 86 may also be affixed to an outer surface 87 of needle 24 and extend from outer surface 87 of needle 24 into recessed area 84. Distal end 85 of lever 74 may extend about post 86 to pull post 86 and, thus, needle 24, proximally within handpiece 22 when lever 74 moves proximally. A first driving spring 90 may be in communication with needle 24 and may further be supported by a fixed portion 91 in handpiece 22.

As trigger button 32 is depressed, linkage 72 may transfer the motion from button 32 to lever 74, causing lever 74 to move proximally within handpiece 22. As lever 74 retracts proximally, first spring 90 may compress due to the contact between lever 74 and spring 90. A trip pin 92 may be affixed to handpiece 22 proximal of lever 74. As lever 74 moves proximally within handpiece 22, angled surface 82 of lever 74 may contact trip pin 92. As lever 74 continues to move proximally under the force of button 32 and linkage 72, the resistance of fixed trip pin 92 may cause lever 74 to pivot about pin 92, lifting distal end 85 of lever 74 away from post 86. As lever 74 rotates away from post 86, post 86 may be released from recessed area 84 of lever 74, thus releasing the stored potential energy in compressed spring 90, which may propel post 86, and thereby needle 24, distally. A return spring 94 may extend from a distal attachment point 96 of lever 74 to a fixed portion of handpiece 22 located below and distal of attachment point 96. After lever 74 is rotated by trip pin 92, return spring 94 may pull against distal attachment point 96 of lever 74 to retract lever 74 back to a horizontal position. As lever 74 retracts, an actuating member return spring 98 may also retract linkage 72 and trigger button 32 back to the first, non-activated position.

Recessed area 84 may comprise a sloped distal face 99 so that as lever 74 is rotated back parallel with needle 24, post 86 may slide underneath sloped distal face 99 and again become lodged within recessed area 84, enabling the needle driving mechanism to be fired again by reactuating trigger button 32. The distance needle 24 travels distally during firing may be varied by adjusting the position of trip pin 92 and post 86.

Figure 9:
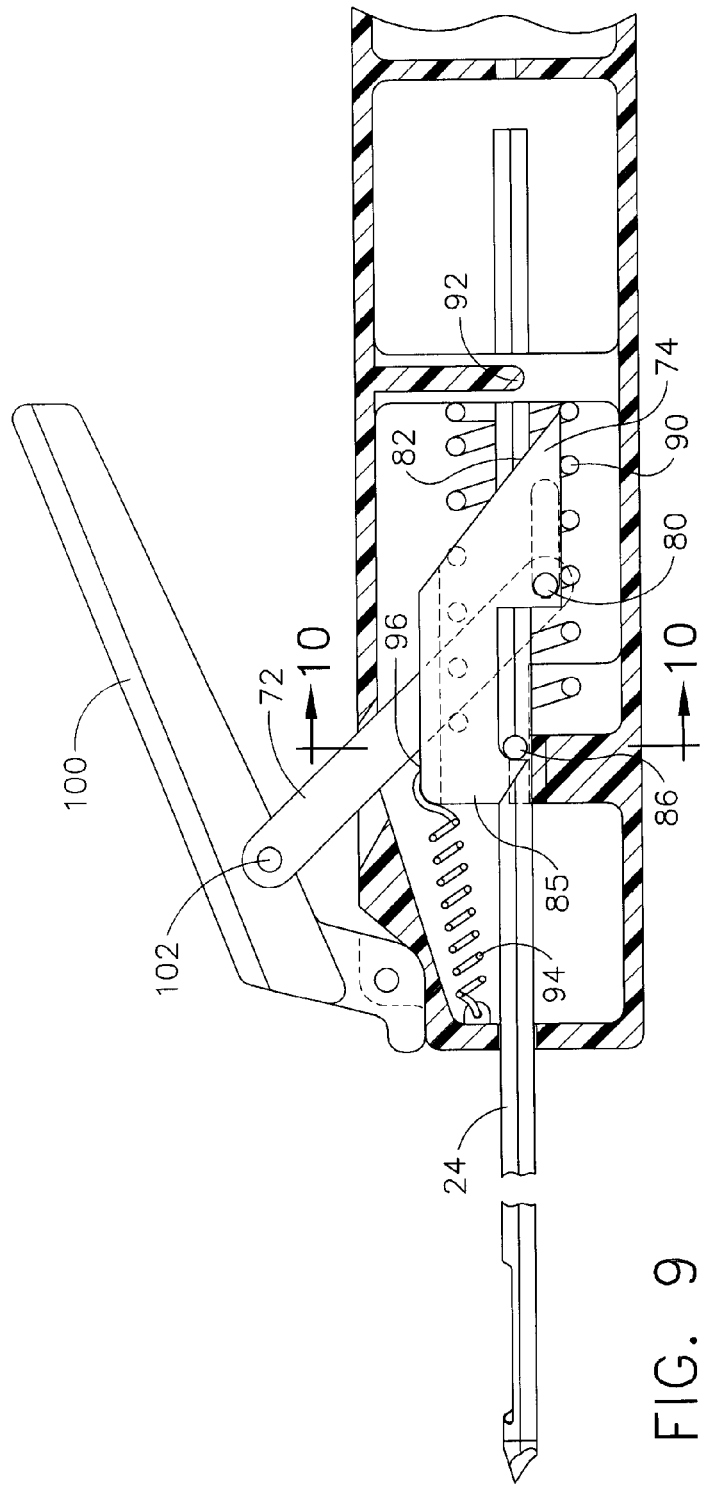
FIG. 9 is a simplified, cross-sectional view of the biopsy instrument of FIG. 1, illustrating an alternative version of a needle driving mechanism similar to that shown in FIG. 7, in which the trigger button is replaced with a handle.
Figure 10:
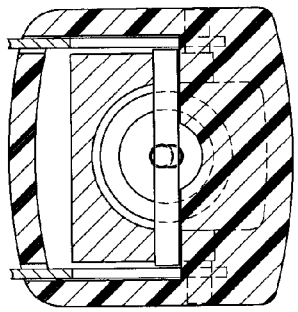
FIG. 10 is a front cross-sectional view of the version shown in FIG. 9.
Figure 11:
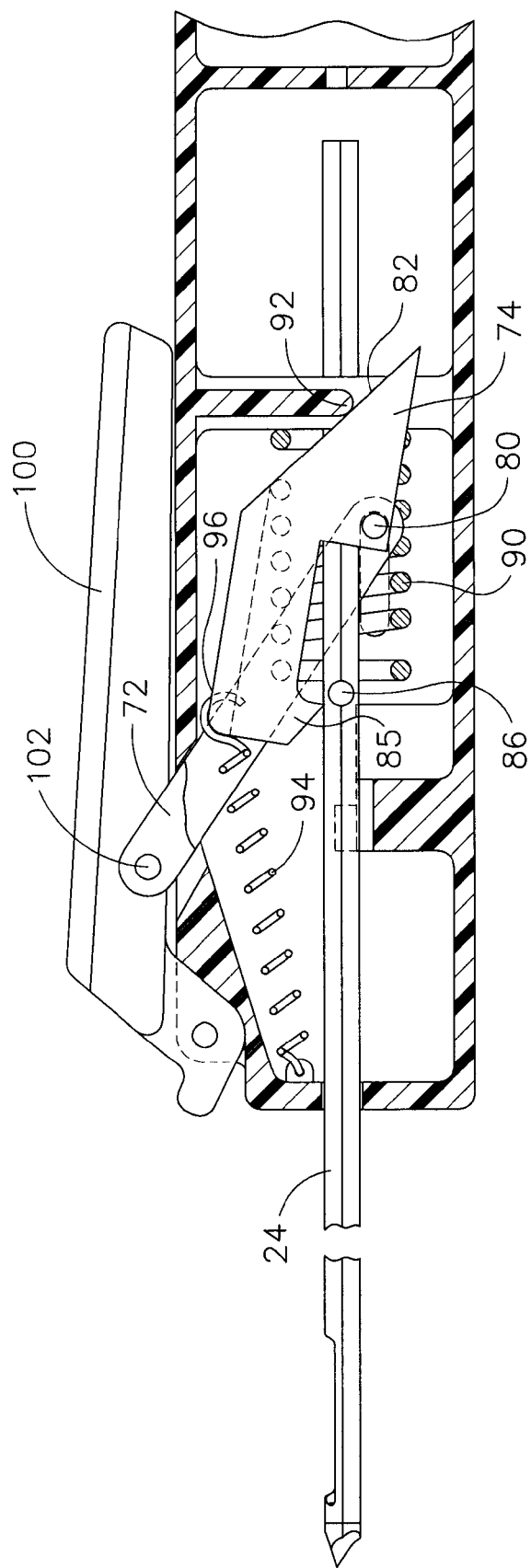
FIG. 11 is a simplified, cross-sectional view similar to FIG. 9, illustrating the needle driving mechanism in an activated position at the point of release of the needle.

The version shown in FIG. 9 is similar to that shown in FIG. 7, with trigger button 32 being replaced with a handle 100. In this version, handle 100 may be pivotally attached to linkage 72 by a pivot pin 102. Linkage 72 may extend from handle 100 to lever 74. When handle 100 is depressed, linkage 72 may push lever 74 proximally within handpiece 22 so that lever 74 may be tripped, and needle 24 fired distally, in the same manner as described above with respect to FIG. 7. Also similar to the version shown in FIG. 4, return spring 94 may be included to return lever 74 to a default position after needle 24 is fired. Handle 100 may then be depressed again to repetitively fire needle 24.

Figure 12:
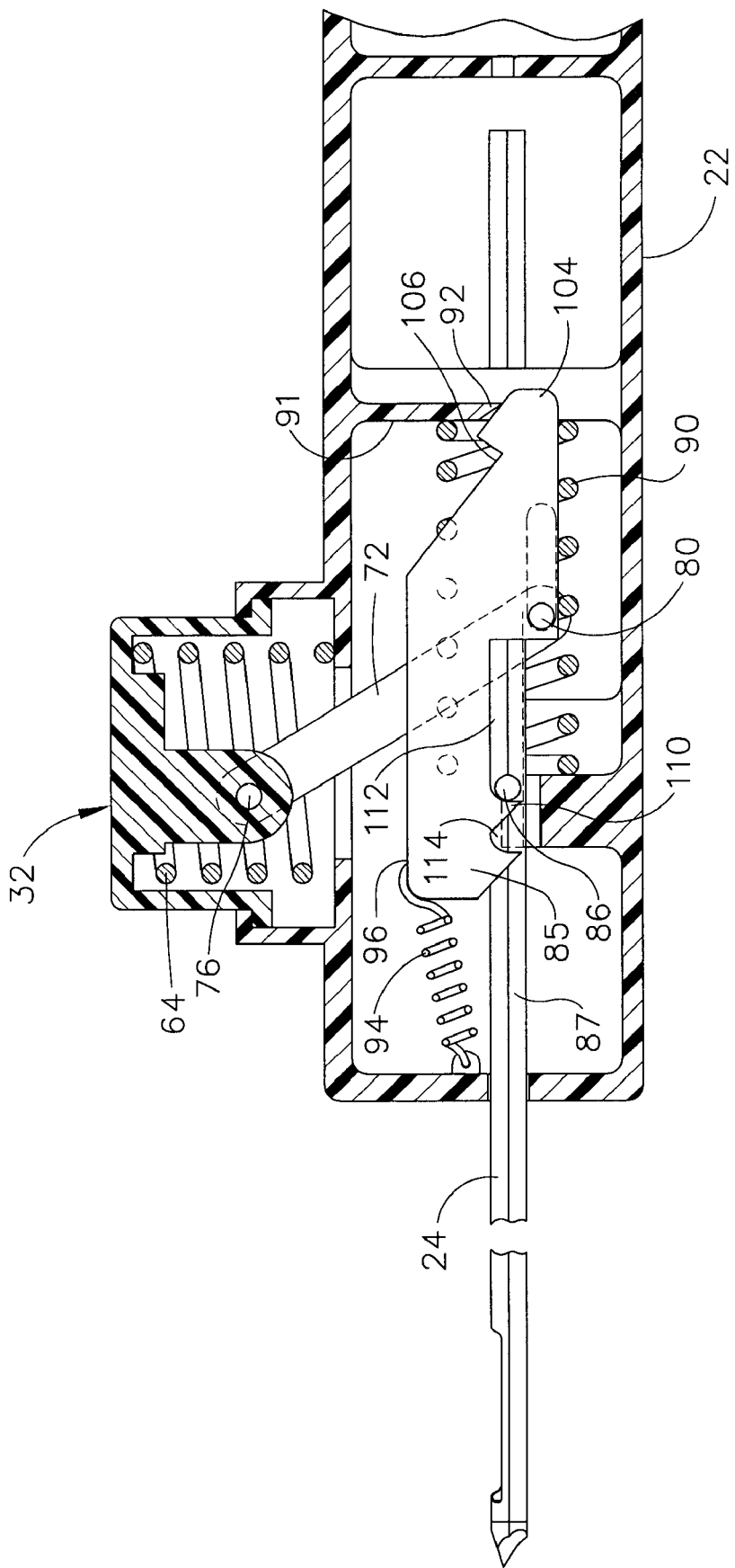
FIG. 12 is a simplified, cross-sectional view of the biopsy instrument of FIG. 1, illustrating an alternative, multiple firing, single stroke needle driving mechanism.
Figure 13:
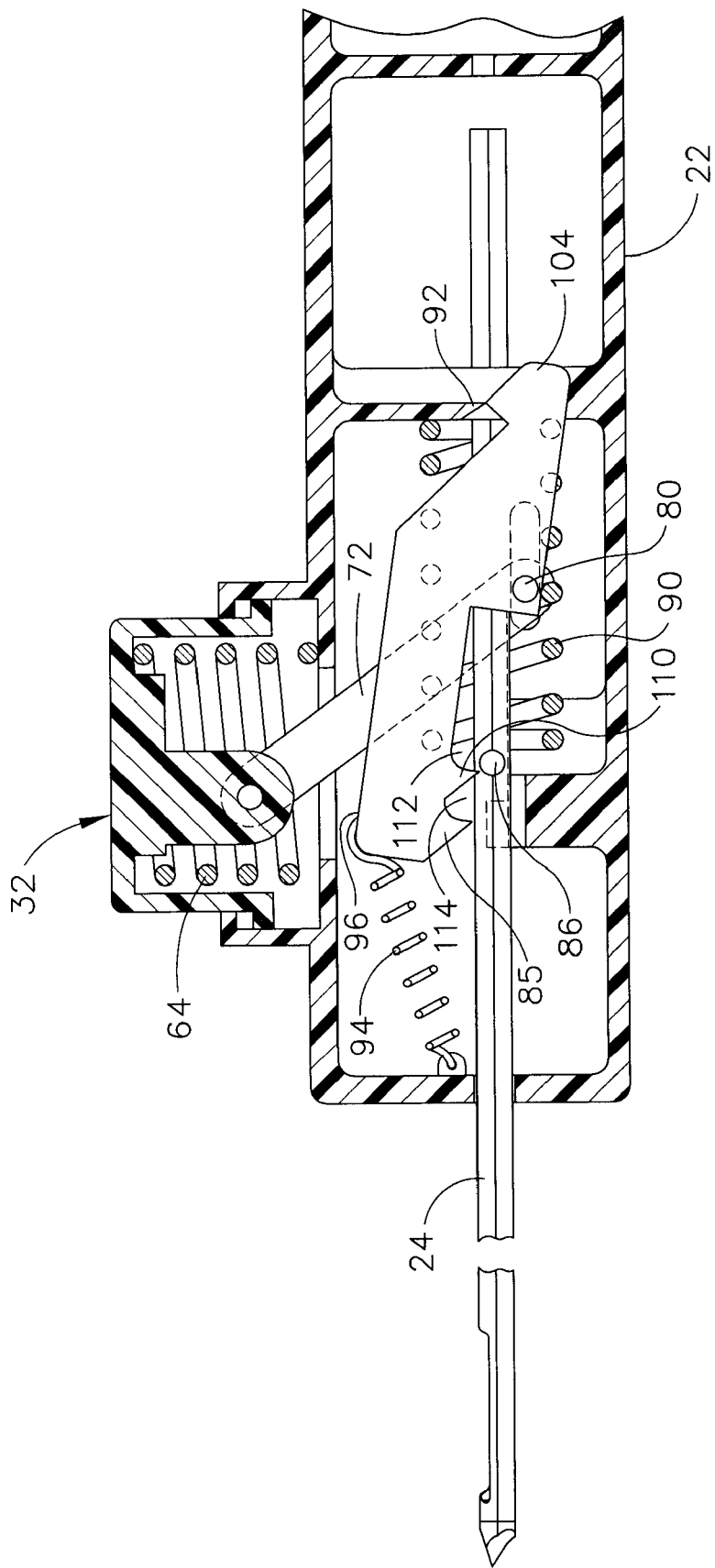
FIG. 13 is a simplified, cross-sectional view similar to FIG. 12, illustrating the multiple firing, single stroke needle driving mechanism in an activated position at a point just prior to release of the needle.
Figure 14:
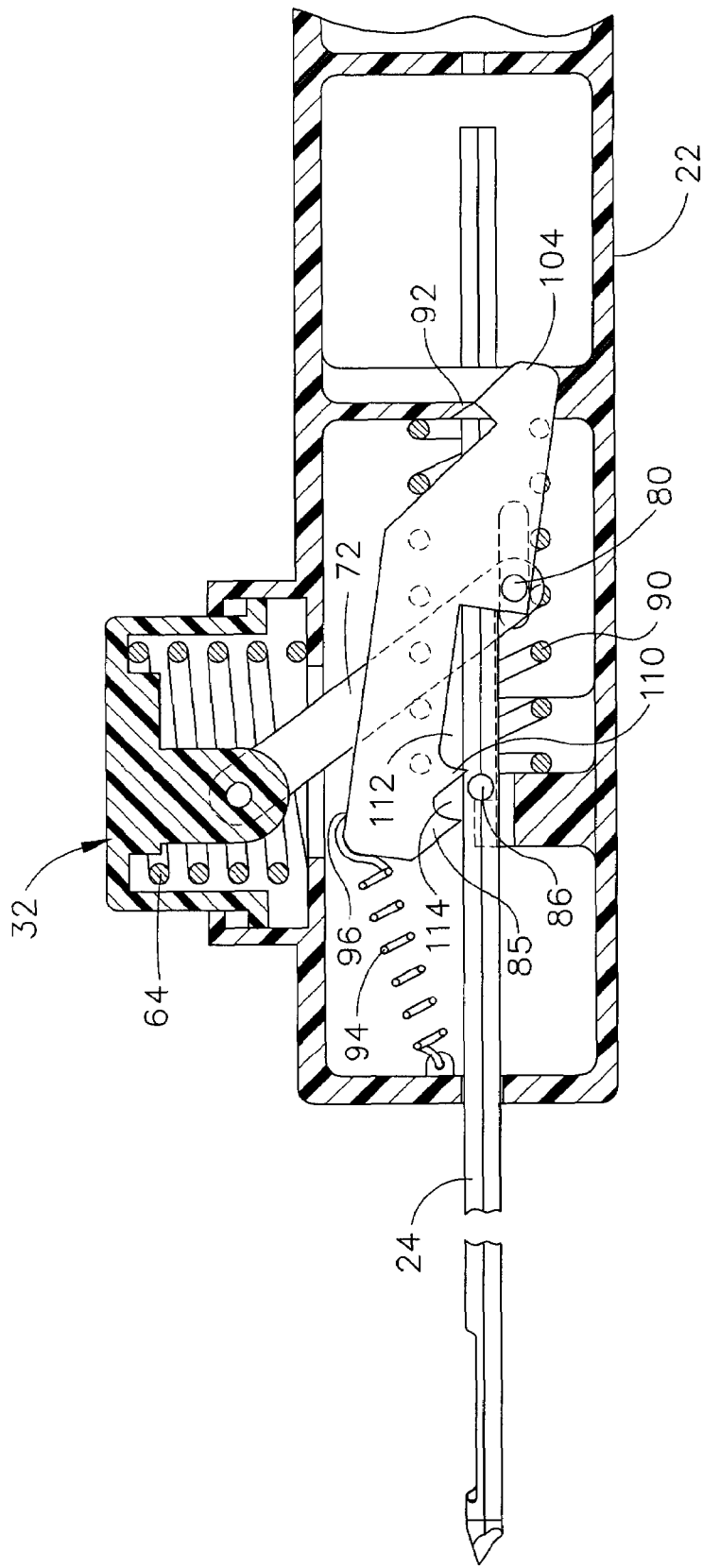
FIG. 14 is a simplified, cross-sectional view similar to FIG. 12, illustrating the multiple firing, single stroke needle driving mechanism in an activated position after initial release of the needle.
Figure 15:
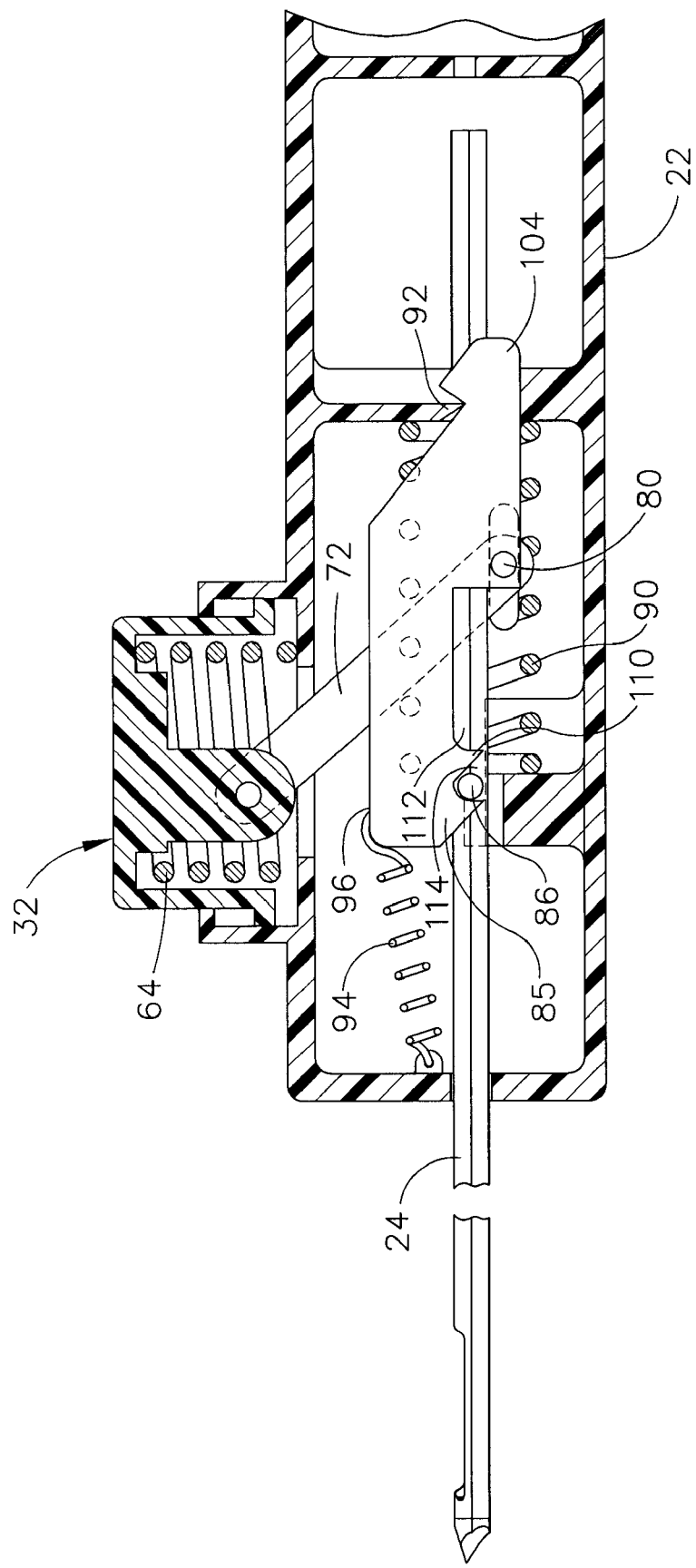
FIG. 15 is a simplified, cross-sectional view similar to FIG. 12, illustrating the multiple firing, single stroke needle driving mechanism in between strokes of the needle.
Figure 16:
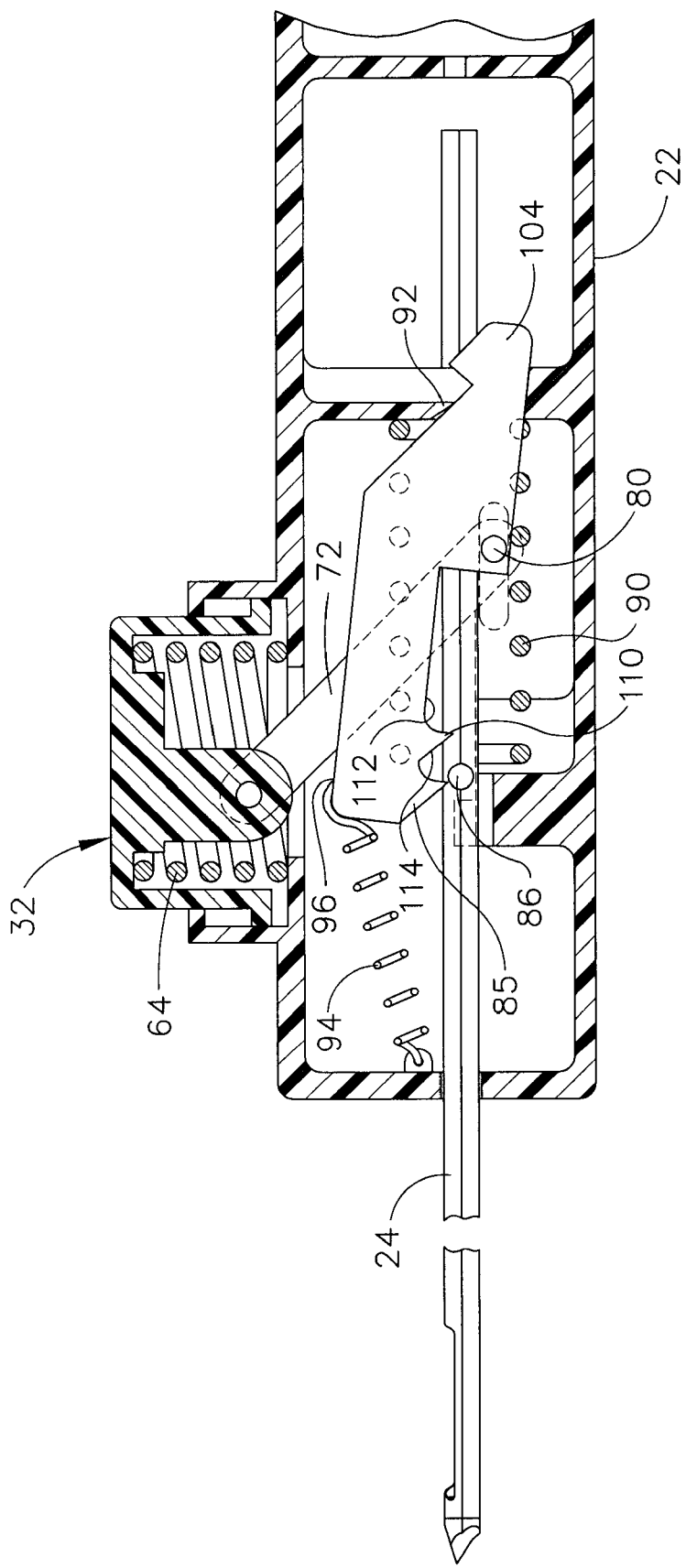
FIG. 16 is a simplified, cross-sectional view similar to FIG. 12, illustrating the multiple firing, single stroke needle driving mechanism at a point just prior to release of the needle for a second stroke.

FIG. 12 illustrates an alternative, multiple firing, single stroke version of the present invention. This version is similar to that illustrated in FIGS. 7 and 9 above, in that a linkage 72 may communicate motion from an actuating member to a lever in order to cock and fire the needle. The firing mechanism of the version shown in FIG. 12, however, may include a lever 104 having one or more notches 106 to allow for multiple firing strokes of needle 24 per single activation of actuating member 32, as will be explained below. Additionally, recessed area 84 may be subdivided by one or more partitions 110 on lever 104. In FIGS. 12-16, recessed area 84 is shown partitioned into two subdivisions 112, 114. As linkage 72 is pivoted by trigger button 32, lever 104 may be driven proximally against trip pin 92. The force against fixed trip pin 92 may cause lever 104 to rotate, releasing post 86 from recess subdivision 112 thereby driving needle 24 distally as shown in FIG. 13. Just after trip pin 92 rides far enough along proximal angled surface 82 of lever 104 to cause lever 104 to rotate enough to allow post 86 to disengage recess subdivision 112, trip pin 92 may be adapted to fall into a first notch 106 of angle surface 82. Return spring 94 may then be adapted to rotate lever 104 towards a horizontal position, thereby catching post 86 in recess subdivision 114 distal of partition 110, as shown in FIG. 15. The force of spring 90, however, may be adapted to cause lever 104 to again rotate about trip pin 92, releasing post 86 from recess subdivision 114 and again driving needle 24 distally, as shown in FIG. 16. Following the release of post 86 from subdivision 114, return spring 94 may substantially act against distal attachment point 96 of lever 104, rotating lever 104 back to a horizontal position. The addition of notches 106 and partitions 110 to lever 104 may enable needle 24 to be driven forward in several short pulses by each activation of trigger button 32. Each movement of post 86 between subdivisions 112, 114 may be adapted to cause an additional impulse force to be imparted to needle 24. It is understood that any number of notches 106 and corresponding partitions 110 may be formed in lever 104 depending upon the desired number of pulsating needle strokes per trigger activation.

Figure 17:
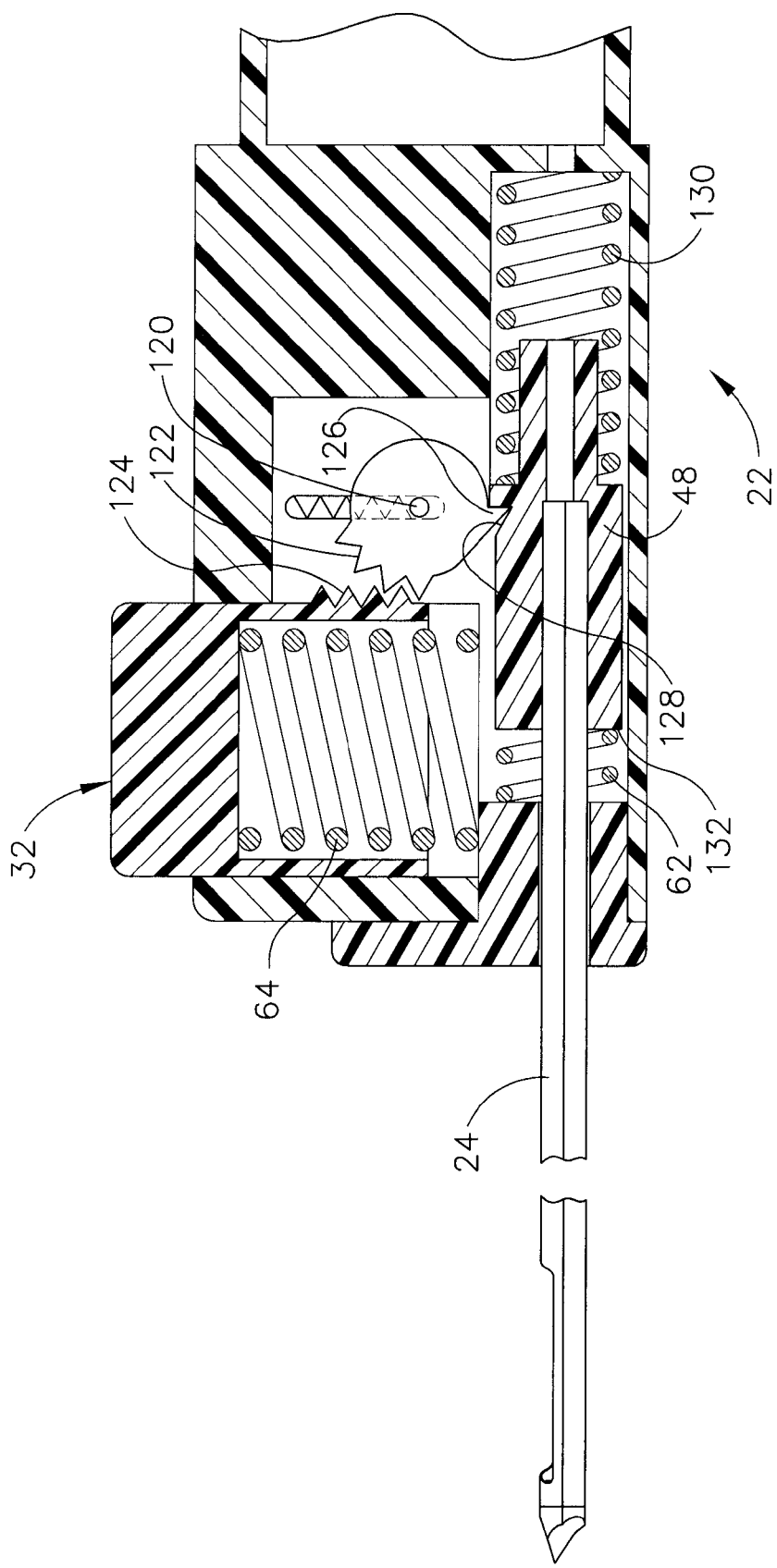
FIG. 17 is a simplified, cross-sectional view of the biopsy instrument of FIG. 1, illustrating an alternative needle driving mechanism utilizing a gear to transfer motion from the trigger button to the needle.
Figure 18:
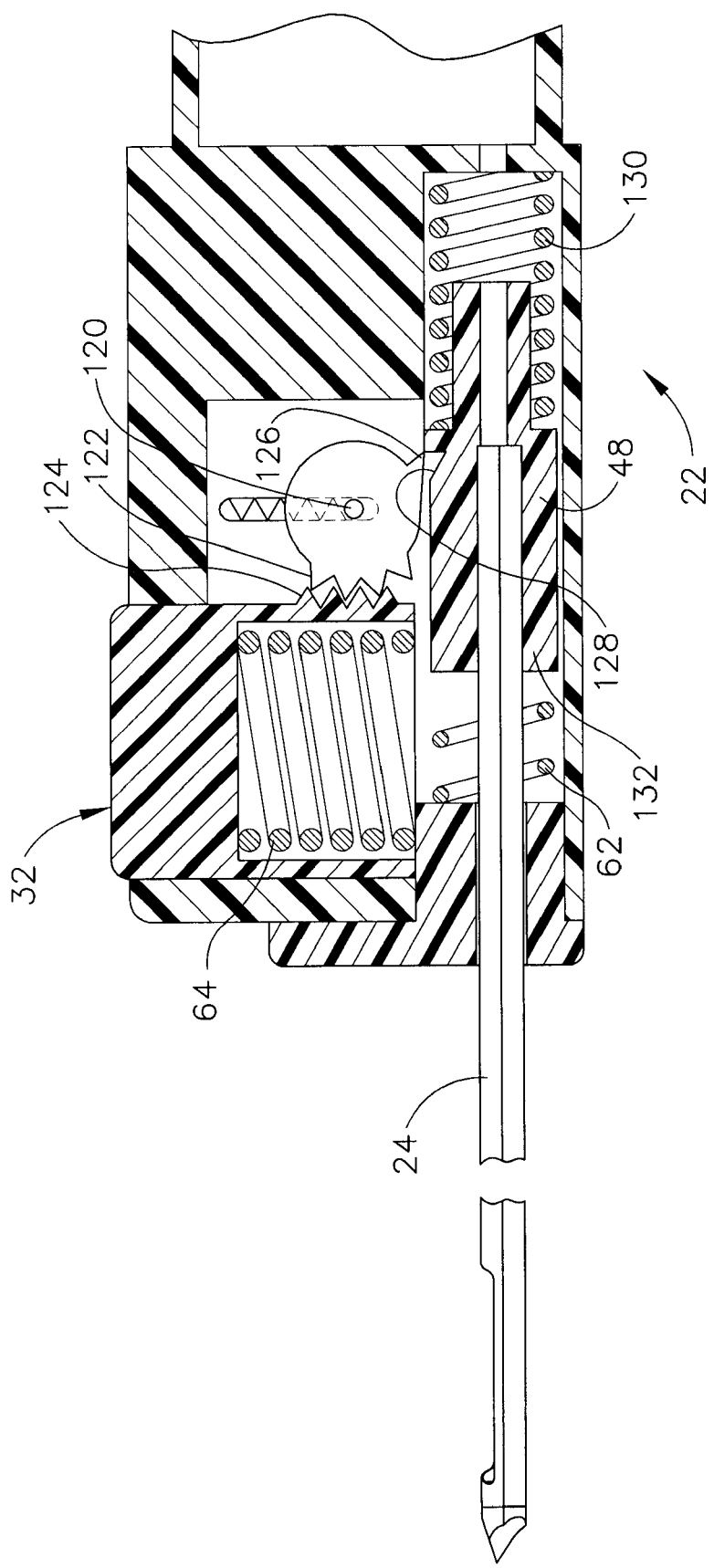
FIG. 18 is a simplified, cross-sectional view similar to FIG. 17, illustrating the needle driving mechanism in the activated position at a point just prior to release of the needle.

FIG. 17 illustrates another version for imparting an impulse driving force to needle 24. In this version, the firing mechanism may comprise a gear 120 that may be utilized to transfer movement of the actuating member (which is shown as a trigger button 32) to needle hub 48. As trigger button 32 is depressed, teeth 122 on gear 120 may be adapted to engage a corresponding series of teeth 124 on trigger button 32. The interaction of gear teeth 122 and trigger button teeth 124 may be adapted to rotate gear 120. Gear 120 may also comprise a trip tooth 126. Trip tooth 126 may be adapted to releasably engage a recess 128 formed on the outer surface 53 of needle hub 48. As trip tooth 126 engages recess 128, gear 120 may drive needle hub 48 proximally within handpiece 22. A spring 130, located proximal of hub 48, may be compressed as hub 48 is retracted by the rotation of gear 120. After proximal retraction of needle hub 48 a predetermined distance within handpiece 22, trip tooth 126 may be adapted to rotate out of engagement with recess 128. Once trip tooth 126 disengages recess 128, the force of compressed spring 130 may be adapted to act against needle hub 48, driving needle 24 distally. As hub 48 is driven distally, dampening spring or pad 62 may compress between distal end 132 of hub 48 and handpiece 22 to absorb the impact sound. As needle 24 moves distally, spring 64 in trigger button 32 may also expand against hub 48, returning trigger button 32 to a non-activated position. In addition to gear 120, additional gearing (not shown) may be added to needle 24 in order to rotate needle 24 in addition to driving it distally.

Figure 19:
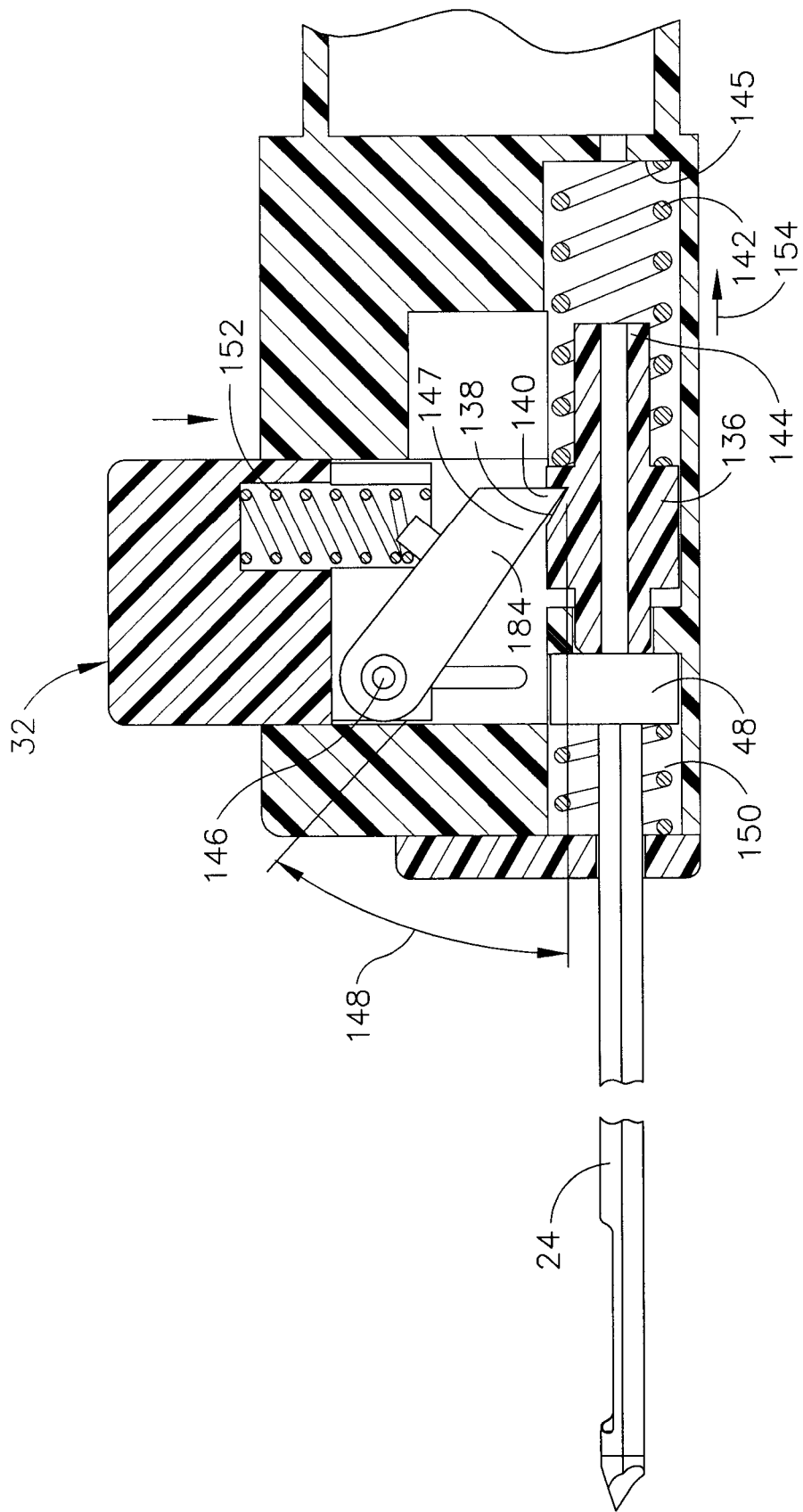
FIG. 19 is a simplified, cross-sectional view of the biopsy instrument of FIG. 1, illustrating an alternative needle driving mechanism that utilizes a driving member to propel the needle distally.
Figure 20:
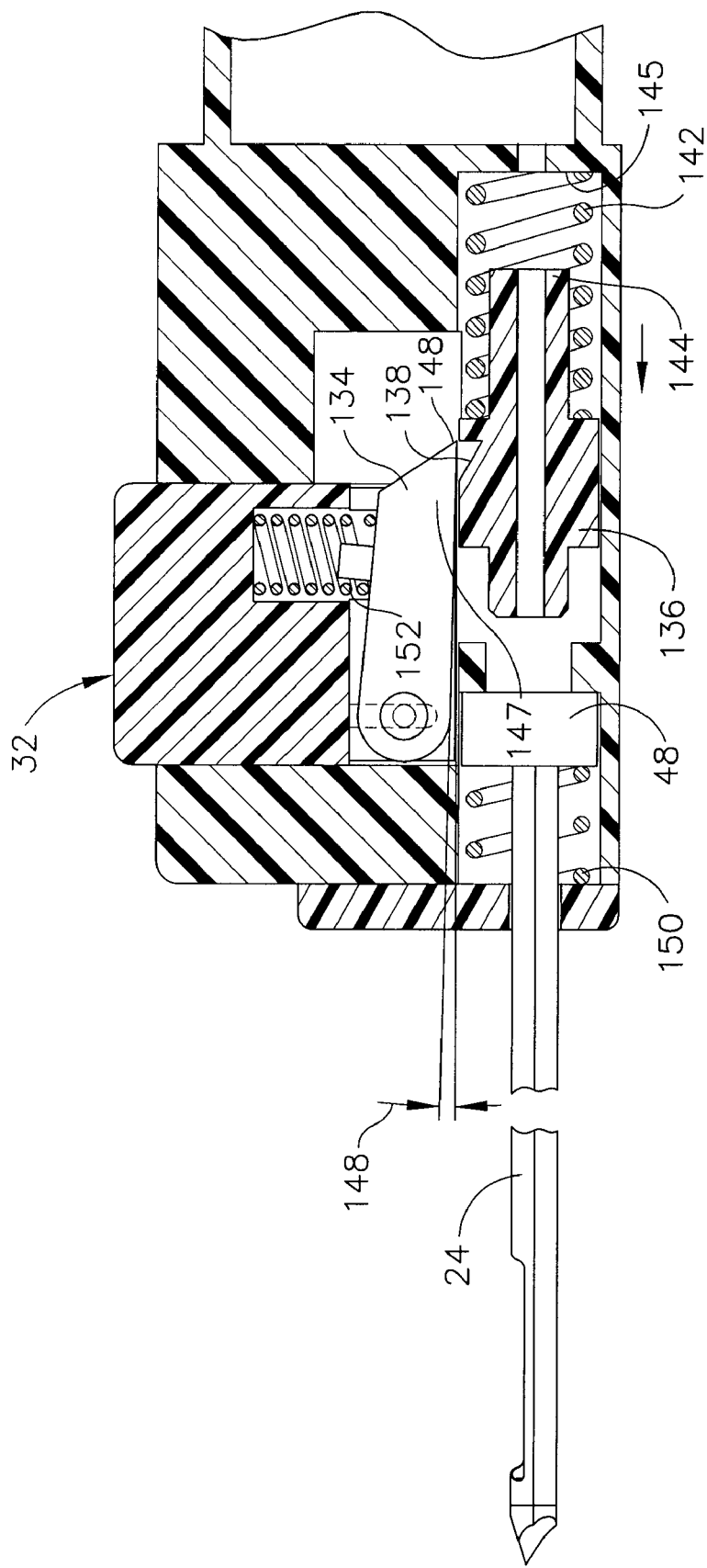
FIG. 20 is a simplified, cross-sectional view similar to FIG. 19, illustrating the needle driving mechanism in an activated position at the point of release of the driving member.
Figure 21:
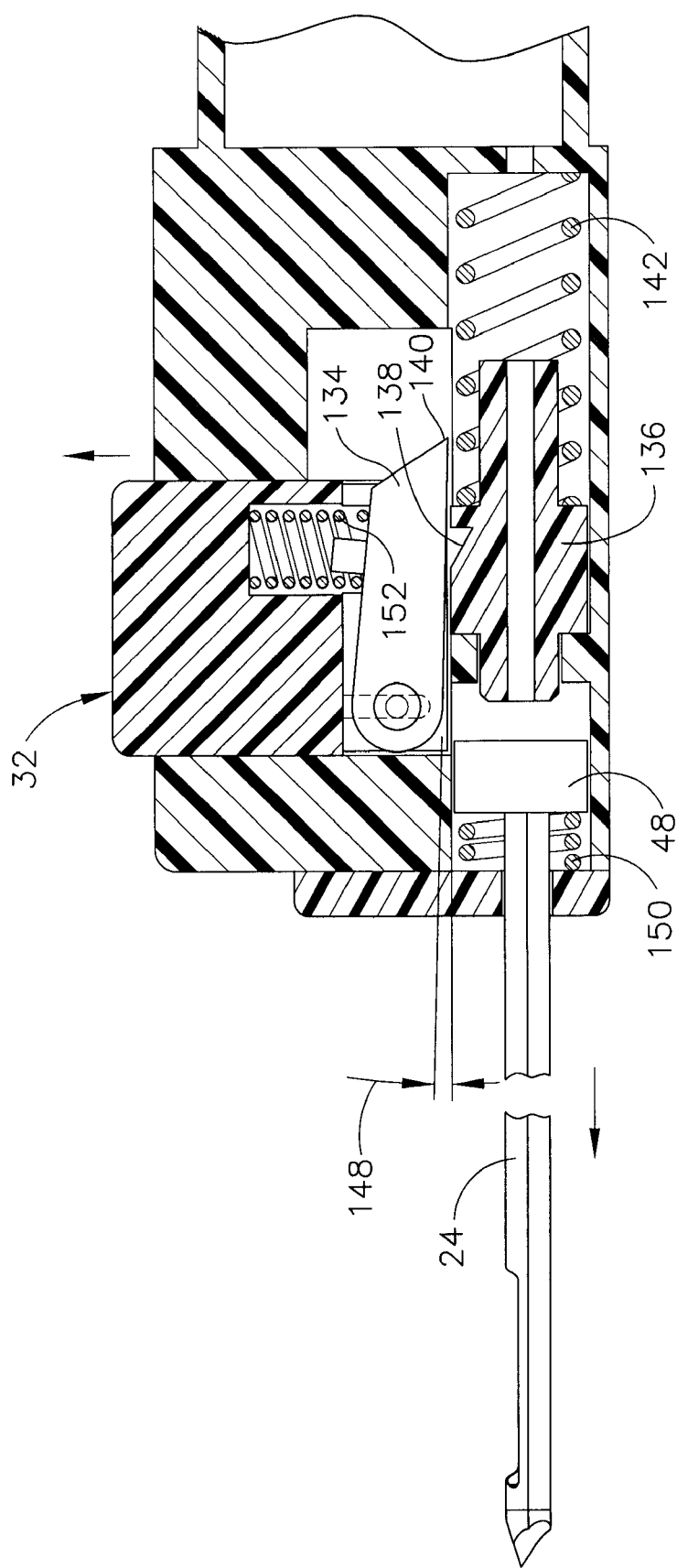
FIG. 21 is a simplified, cross-sectional view similar to FIG. 20, illustrating distal motion of the needle due to propulsion by the driving member.

FIGS. 19-21 illustrate another version consistent with the present invention for imparting an impulse force to needle 24. In the version shown in FIG. 19, the firing mechanism may comprise a driving arm 134 extending from the actuating member (shown as a trigger button 32) to a driving element 136 located proximal of needle 24 and hub 48 within handpiece 22. Driving element 136 may include a recessed area 138 that engages a protusion 140 on arm 134, in a manner similar to that described above with respect to the version shown in FIG. 3. A first spring 142 may be in communication with a proximal end 144 of driving element 136 to extend proximally between driving element 136 and a fixed partition 145 within handpiece 22. As shown in FIG. 20, as trigger button 32 is depressed, arm 134 may pivot about a pin 146, causing an opposing end 147 of arm 134 to move proximally within handpiece 22. As arm 134 moves proximally, the interaction between protrusion 140 and recess 138 may be adapted to pull driving element 136 in a proximal direction, as indicated by arrow 154. The proximal movement may decrease an angle 148 between arm 134 and driving element 136. Spring 142 may be compressed as driving element 136 moves proximally.

Arm 134 may be adapted to continue to rotate until reaching a point where protrusion 140 is adapted to disengage from recess 138. As arm 134 disengages from driving element 136, as shown in FIG. 21, spring 142 may be adapted to release its stored energy against driving element 136, forcing driving element 136 distally to impact against needle hub 48. Driving element 136 may be weighted to increase the force of its impact against needle hub 48. The impact of driving element 136 against needle hub 48 may force needle 24 forward. In order to provide driving element 136 with sufficient impact force to adequately drive needle hub 48, driving element 136 may be comprised of a dense material, such as stainless steel. Further, because needle hub 48 must withstand the impact of driving member 136, it may be comprised of stainless steel or some other dense material. It is recognized, however, that driving element 136 and needle hub 48 may comprise numerous suitable materials. The device 20 may further comprise a second spring 150 in communication with needle 24 distal of hub 48. As the momentum of element 136 drives hub 48 forward, second spring 150 may compress between hub 48 and housing 22. When the momentum of driving element 136 is transferred to the tissue via needle 24, second spring 150 may provide resistance against needle hub 48, pushing needle 24 proximally back within handpiece 22. As driving element 136 is drawn proximally by the combination of spring forces, and trigger button 32 is returned from the second, non-activated position to the first, activated position by the force of a return spring 164, protrusion 140 may be adapted to reengage recess 138. The needle driving mechanism may, thus, reset for additional firing, enabling the driving mechanism to be actuated and fired multiple times to produce a pulsating motion in the needle. In this version, actuating trigger button 32 may be adapted to impart a forward-then-backward penetration force to needle 24.

Figure 22:
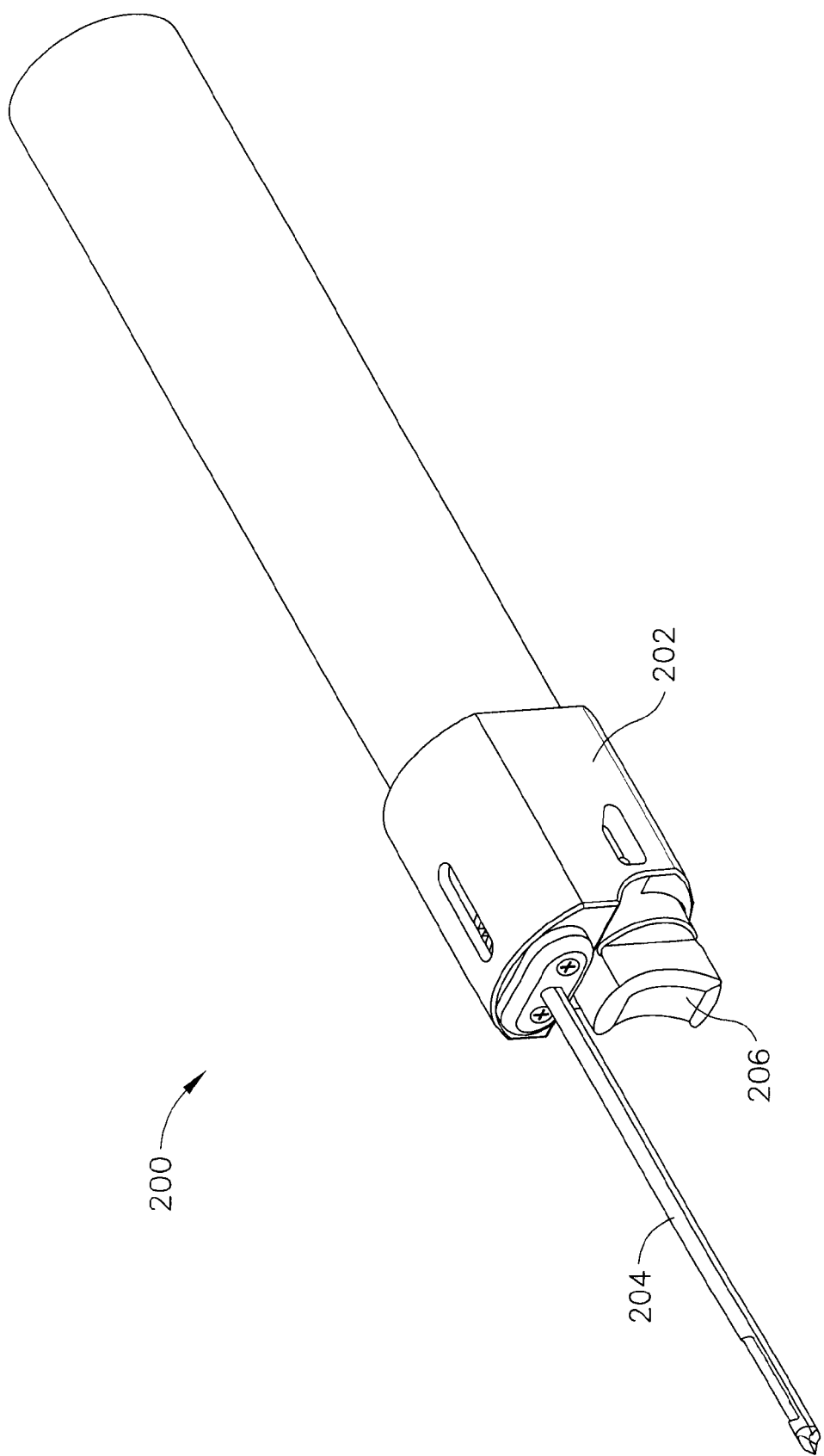
FIG. 22 is a perspective view of a representative biopsy instrument incorporating the needle driving mechanism of the present invention in which the actuating member is a trigger button located on the distal face of the instrument.
Figure 23:
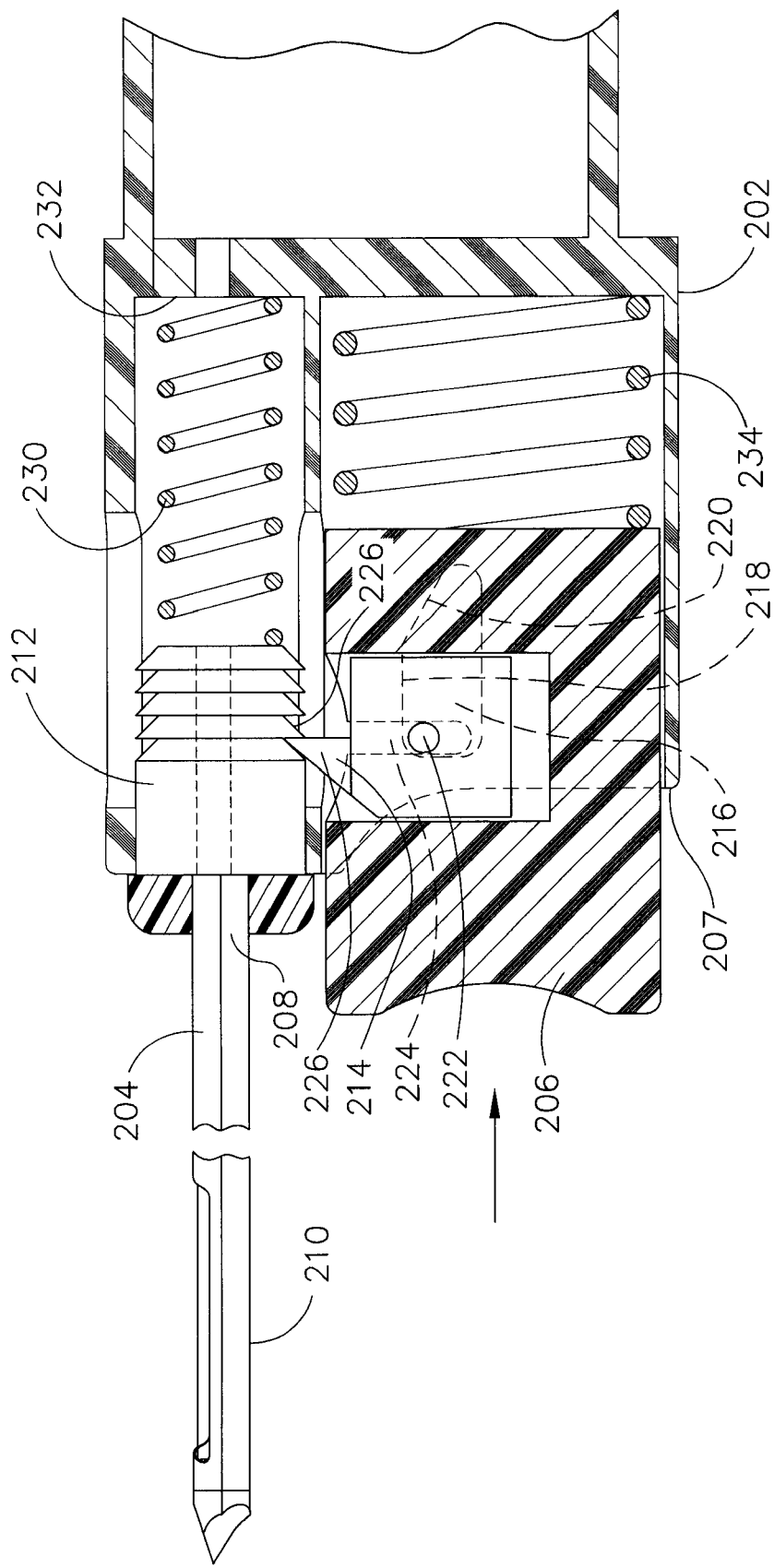
FIG. 23 is a simplified, cross-sectional view of one version of the biopsy instrument of FIG. 22.
Figure 24:
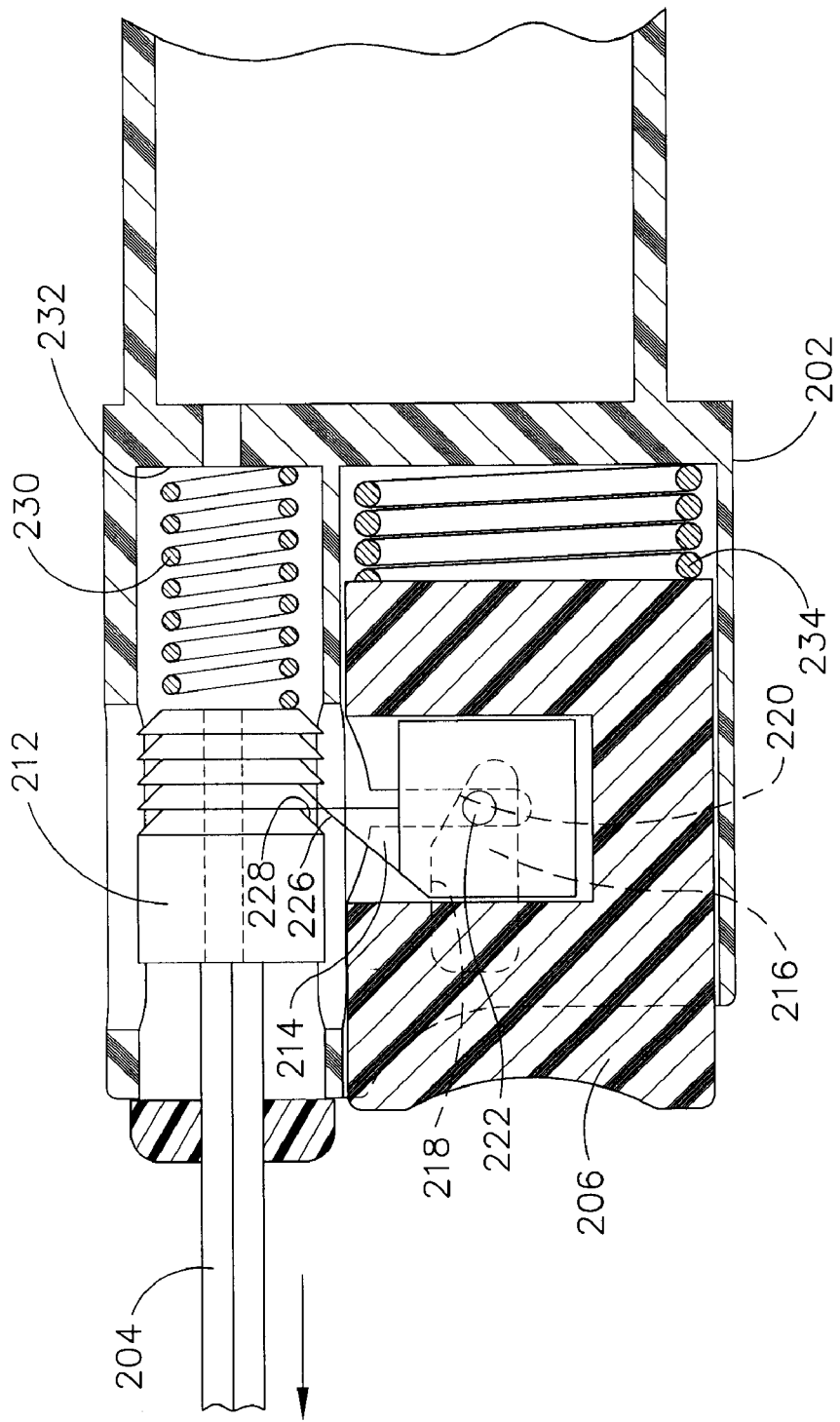
FIG. 24 is a simplified, cross-sectional view similar to FIG. 23, illustrating the needle driving mechanism at a point just prior to release of the needle.

FIG. 22 illustrates an alternative version for a biopsy instrument 200 comprising a housing 202 and a needle 204 in which the firing mechanism may comprise an actuating member, shown as a trigger button 206. Trigger button 206 may be located on a distal face 207 of housing 202. FIG. 23 is a simplified cross-sectional view of the instrument shown in FIG. 22, depicting yet another version of a needle driving mechanism in accordance with the present invention. Needle 204 may comprise a proximal portion 208 and a distal portion 210. Needle 204 may further be attached at its proximal portion 208 to a needle hub 212. Needle hub 212 may be adapted to retain proximal portion 208 of needle 204 within housing 202.

In the firing mechanism shown in FIG. 23, a lever 214 may be adapted to transfer motion from trigger button 206 to needle hub 212. Housing 202 may include an opening 216 having an upper surface 218 comprising an angled proximal surface 220. A guide pin 222 may extend from a first end 224 of lever 214 into opening 216. An opposite end 226 of lever 214 may be triangular-shaped and may be adapted to engage one of several similarly shaped grooves 228 on needle hub 212.

When trigger button 206 is depressed, lever 214 and guide pin 222 may be adapted to move proximally within housing 202. Needle hub 212 may be adapted to move proximally in conjunction with lever 214 due to the engagement of triangular end 226 of lever 214 with groove 228. A first spring 230 may be located between needle hub 212 and a fixed wall 232 of housing 202. Spring 230 may compress as hub 212 moves proximally within housing 202.

As lever 214 moves proximally, guide pin 222 may be adapted to ride along upper surface 218 of opening 216 and down angled proximal surface 220. As guide pin 222 rides down angled proximal surface 220, triangular end 226 of lever 214 may be adapted to disengage groove 228 in order to release hub 212 from lever 214. When needle hub 212 is released from lever 214, the force of spring 230 may propel needle 204 distally from housing 202. After hub 212 is released, a second spring 234 that may be located proximal of trigger button 206 may expand to return button 206 to a non-activated position. As button 206 returns to a non-activated position, lever 214 may be adapted to reengage groove 228 on hub 212 to enable the needle driving mechanism to be refired. In this version, actuating trigger button 206 may be adapted to impart a backward then forward penetration force to needle 204.

Figure 25:
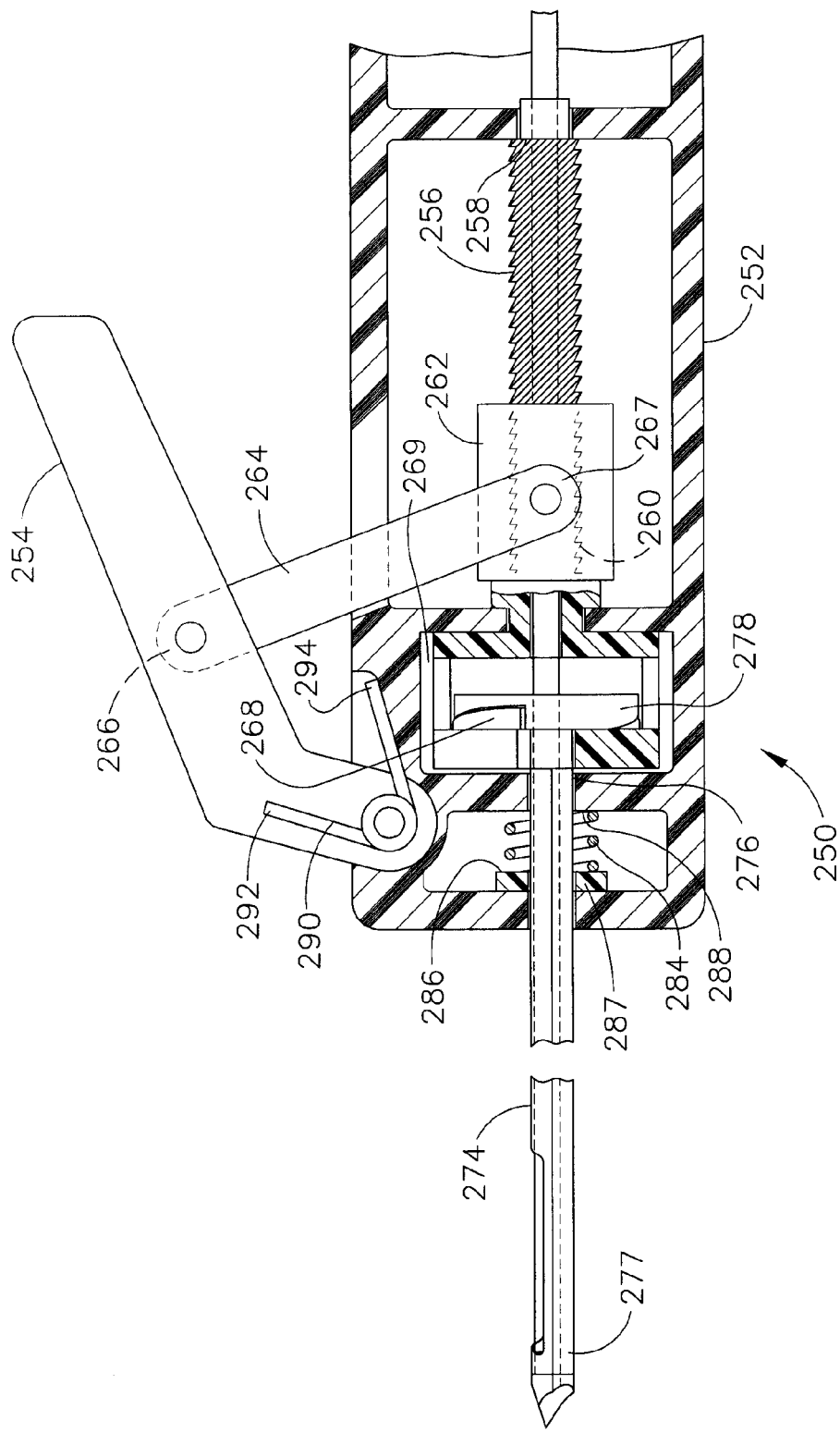
FIG. 25 is a simplified, cross-sectional view of the biopsy instrument of FIG. 1, illustrating an alternative version of a single fire, multi-stroke needle driving mechanism.
Figure 26:
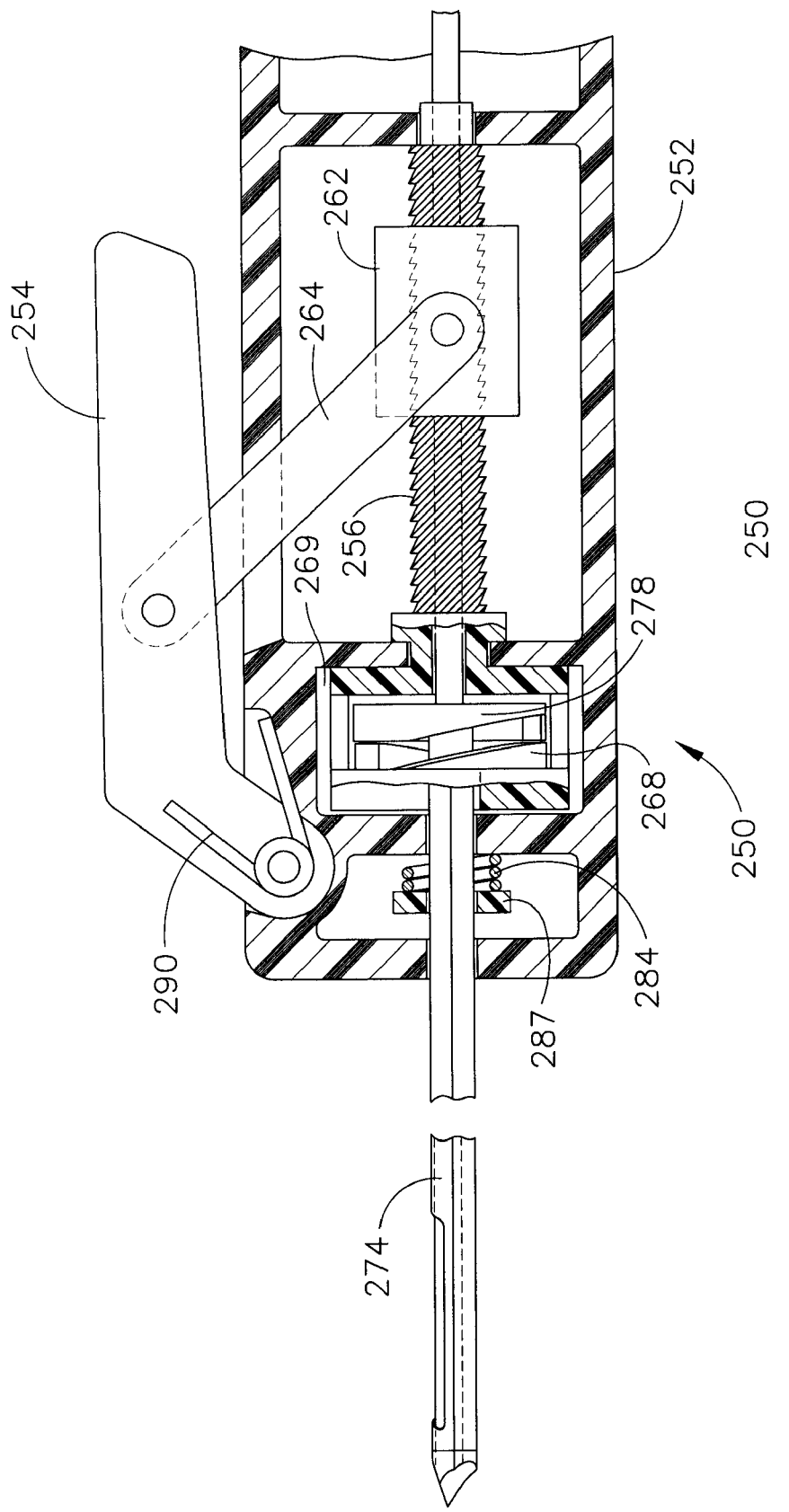
FIG. 26 is a simplified, cross-sectional view similar to FIG. 25, illustrating the needle driving mechanism in an extended position.

FIG. 25 illustrates yet another alternative version consistent with the present invention. In this version, a biopsy instrument 250 may comprise a housing 252. The firing mechanism may comprise an actuating member that may be moveable from a first, non-activated position to a second, activated position. In FIG. 25, the actuating member is shown as a handle 254. However, the actuating member may comprise any other type of button, switch, lever or knob that can be manually operated with a single human hand while simultaneously holding the handpiece. The firing mechanism may also comprise a lead screw 256 having a proximal end 258 and a distal end 260. Lead screw 256 may be rotatably attached to housing 252. Lead screw 256 may be aligned with the longitudinal axis of housing 252.

Biopsy instrument 250 may also comprise a nut 262 that is adapted to ride on lead screw 256. Nut 262 may be adapted to engage handle 254. In one version, nut 262 may engage actuating member 254 by a linking member 264 comprising a first end 266 that is pivotally connected to actuating member 254 and a second end 267 that is pivotally connected to nut 262.

Figures 27A, 27B:
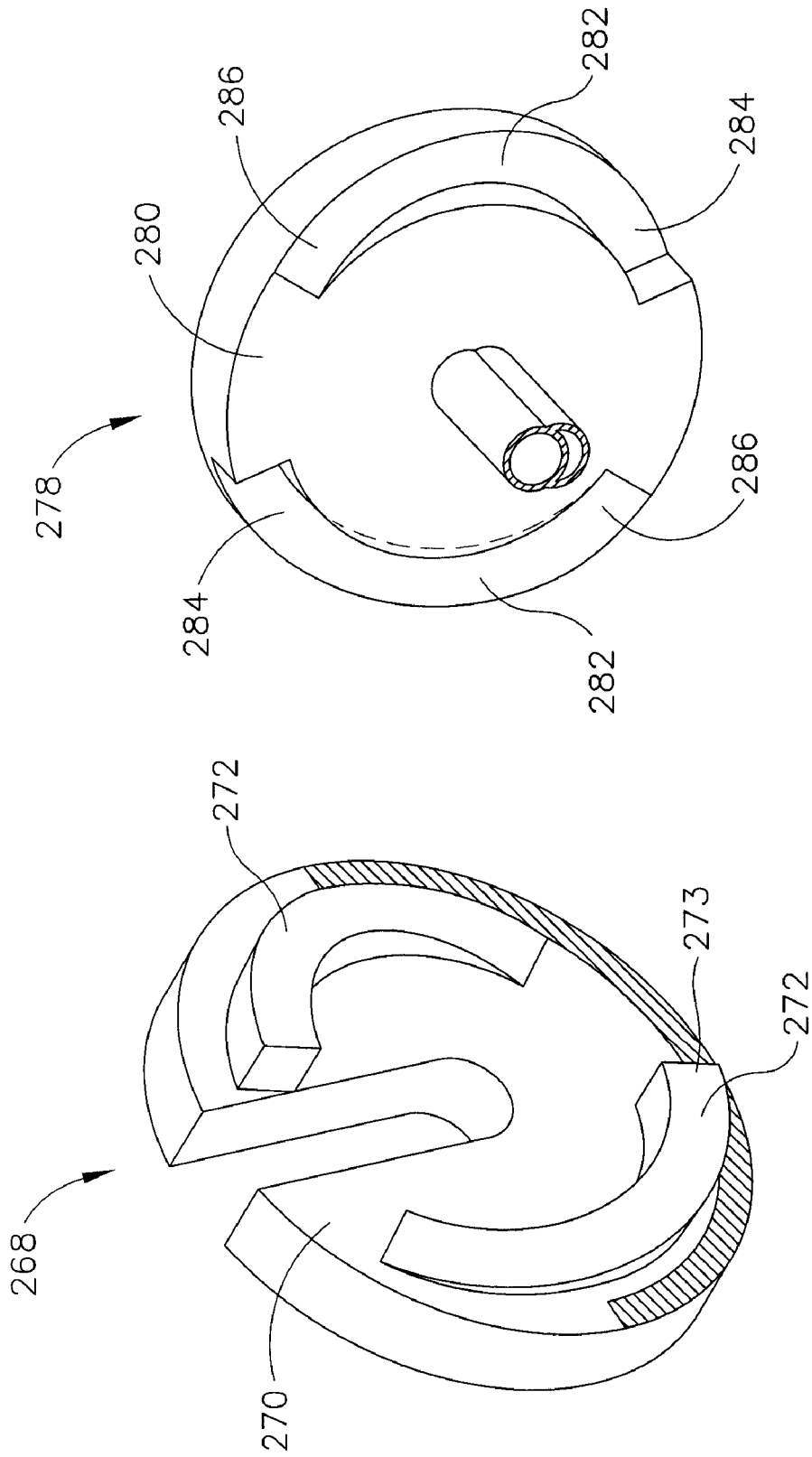
FIG. 27A is a perspective view of the first cam of the version of the biopsy instrument of FIG. 25.
FIG. 27B is a perspective view of the second cam of the version of the biopsy instrument of FIG. 25.

Biopsy instrument 250 may further include a first cam 268 that may be fixed to a cam box 269, which may be fixed to distal end 260 of lead screw 256 such that rotation of lead screw 256 also causes first cam 268 to rotate. First cam 268 may include a proximal face 270. Proximal face 270 may comprise an uneven surface. FIG. 27A shows one version of first cam 268 in which the uneven surface is comprised of a pair of curved ramps 272. However, the uneven surface of first cam 268 may comprise various terrains.

Biopsy instrument 250 may further include a needle 274 having a proximal portion 276 and a distal portion 277. Needle 274 may be retained at its proximal portion 276 within housing 252. As shown in FIG. 25, a second cam 278 may be fixedly attached to proximal portion 276 of needle 274. As best pictured in FIG. 27B, second cam 278 may comprise a distal face 280. Distal face 280 may comprise an uneven surface. In one version, as shown in FIG. 27B, uneven surface 280 of second cam 276 may comprise a pair of curved ramps 282. However, the uneven surface of second cam 278 may comprise various terrains. Curved ramps 272 of first cam 268 may be adapted to rotate against curved ramps 282 of second cam 278.

Biopsy instrument 250 may further comprise a needle return spring 284 comprising a first end 286 in communication with a needle hub 287 of needle 274 and a second end 288 in communication with housing 252. Biopsy instrument 250 may also include an actuating member return spring 290 comprising a first end 292 in communication with actuating ember 254 and a second end 294 in communication with housing 252.

Movement of handle 254 from the first, non-activated position to the second, activated position may cause nut 262 to ride proximally along the length of lead screw 256. Movement of nut 262 along lead screw 256 may force lead screw 256 to rotate, thereby causing first cam 268 to rotate as well. Rotation of first cam 268 may cause curved ramps 272 of first cam 268 to rotate against curved ramps 282 of second cam 278. As curved ramps 272, 282 of first cam 268, second cam 278, respectively, rotate against one another, second cam 278 may be alternately pushed away from first cam 268, then brought closer to first cam 268, as the point in the rotation of curved surfaces 272, 282 allow the biasing force of needle return spring 284 to push first and second cams 268, 278 closer together. Since needle 274 may be attached to second cam 278, this alternating motion may have the effect of alternately moving needle 274 proximally and distally multiple times per activation of handle 254.

In one aspect, device 250 may be oriented such that in its default position, a leading edge 273 of each of curved ramps 272 of first cam 268 is aligned with a leading edge 284 of each of curved ramps 282 of second cam 278. In this aspect, as handle 254 is engaged, causing lead screw 256 to rotate, leading edges 284 of curved ramps 272 may rotate against curved ramps 282 of second cam 278, pushing needle 274 proximally within device 250. Further, when leading edges 273 of curved ramps 272 reach an end 286 of the respective curved ramps 282, leading edges 273 of first cam 268 may travel across distal face 280 of second cam 278 until falling into leading edge 284 of the opposite curved ramp 282, thereby causing needle 274 to move distally within device 250. This motion is repeated as handle 254 is depressed.

In another aspect, first cam 268 may be attached to needle 274 and second cam 278 may be attached to cam box 269. In this aspect, needle 274 may be pushed proximally upon initial actuation of handle 274, followed by a return to the default position, a cycle that may be repeated multiple times by a single actuation of handle 254.

Actuating member return spring 290 may function to return actuating member 254 from the second, activated position, to the first, non-activated position, readying the instrument 250 to be fired again. Due to the interaction between first and second cams 268, 278, biopsy instrument 250 may provide multiple reciprocations of needle 274 with a single movement of actuating member 254 between the first, non-activated position and the second, activated position.

While several versions of the present invention have been shown and described herein, it will be obvious to those skilled in the art that such versions are provided by way of example only. In addition to the above-described versions, other mechanisms may also be utilized to produce a controlled impulse motion in a biopsy needle in accordance with the present invention. These mechanisms may include, without limitation, a pneumatic drive system for imparting a pneumatic force to the needle, a motor-driven mechanism, a magnetic system and a harmonic system. Accordingly, it is understood that numerous variations, changes, and substitutions to the present invention will occur to those skilled in the art without departing from the spirit and scope of the appended claims.

What is claimed is:

1. A reciprocating needle biopsy device, comprising:
   (i) a housing;
   (ii) a needle having a proximal portion and a distal portion, said needle being slidably retained at said proximal portion thereof within said housing, wherein the needle has a closed distal tip;
   (iii) a firing mechanism adapted to releasably engage said needle, said firing mechanism comprising a firing member and a first spring configured to move said needle longitudinally in a distal direction, from a default position to a release position, wherein the release position is distal to the default position, wherein further said firing mechanism is adapted to disengage said needle at said release position, wherein said firing member is configured to move within said housing between a first position and a second position, wherein said first position is located distally of said second position, wherein said first spring comprises a first portion in communication with said firing member and a second portion in communication with a fixed portion of said housing, such that said first spring is adapted to store potential energy when said firing member is moved proximally within said housing from said first position to said second position, wherein further said first spring is adapted to convert the stored potential energy to kinetic energy, by urging the firing member distally, once the firing member reaches the second position;
   (iv) an actuating member, wherein the actuating member is configured to actuate the firing mechanism, wherein the actuating member is configured to releasably engage the firing member, wherein the actuating member is configured to disengage the firing member at the second position; and
   (v) a second spring comprising a first portion in communication with said needle and a second portion in communication with a fixed portion of said housing, such that said second spring is adapted to store potential energy when said needle is moved in the distal direction from said default position to said release position, wherein further said second spring is adapted to convert the stored potential energy to kinetic energy, by urging the needle proximally, once said needle disengages said firing mechanism;
   wherein actuation of the firing mechanism performs a sequential action of moving the firing member in a proximal direction within the housing from the first position to the second position, while storing potential energy in the first spring, immediately followed by disengagement of the actuating member from the firing member once the firing member has reached the second position, thereby enabling the firing member to move distally toward the needle under the urging of the first spring, immediately followed by the firing member engaging the needle and moving said needle, in a distal direction, away from the housing, from the default position to the release position while storing potential energy in said second spring immediately followed by disengagement of the firing member from said needle enabling immediate return of said needle from the release position to the default position, in a proximal direction, opposite to the distal direction and toward the housing, under the urging of said second spring to complete a first reciprocating motion of said needle.

2. The reciprocating needle biopsy device of claim 1, said actuating member being moveable from a first, non-activated position to a second, activated position.

3. The reciprocating needle biopsy device of claim 2, wherein said actuating member comprises a select one of a group consisting of a trigger button and a handle.

4. The reciprocating needle biopsy device of claim 1, further comprising a return spring adapted to re-engage said actuating member with said firing member.

5. The reciprocating needle biopsy device of claim 4, wherein said proximal portion of said needle is fixedly attached to a hub having an outer surface, wherein said hub is moveable from a default position to a release position.

6. The reciprocating needle biopsy device of claim 1, wherein said needle is adapted to move less than 0.5 inches between said release position and said default position.

7. The reciprocating needle biopsy device of claim 6, wherein said needle is adapted to move less than 0.2 inches between said release position and said default position.

8. The reciprocating biopsy needle device of claim 1, wherein said proximal portion of said needle comprises a hub.

9. The reciprocating biopsy needle device of claim 8, wherein said firing arm further comprises a protrusion adapted to releasably engage a recess of said hub.

10. The reciprocating biopsy needle device of claim 1, further comprising a cutter element that is adapted to advance distally through said needle independently of said firing mechanism.

11. The reciprocating needle biopsy device of claim 1, wherein the actuating member is configured to be actuated multiple times to allow the needle to reach a desired portion of tissue.

12. The reciprocating needle biopsy device of claim 1, wherein said actuating member is moveable from a first, non-activated position to a second, activated position, wherein said firing mechanism comprises:
  a linking member having a first end and a second end, wherein said first end is pivotally connected to said actuating member and said second end is releasably engaged with said firing member;
  wherein said linking member is adapted to transfer motion from said actuating member to said firing member when said actuating member is moved from said first, non-activated position to said second, activated position, causing said firing member to move from said first position to said second position, thereby storing potential energy in said first spring;
  wherein said linking member is further adapted to disengage said firing member at said second position, releasing the stored potential energy in the spring.

13. The reciprocating needle biopsy device of claim 12, wherein said firing member further comprises a recess on an outer surface thereof and an angled proximal edge.

14. A reciprocating needle biopsy device, comprising:
  (i) a housing comprising an actuating member, said actuating member being moveable from a first, non-activated position to a second, activated position;
  (ii) a driving arm comprising a first end and a second end, wherein said first end is pivotally attached to said actuating member, such that movement of said actuating member from said first, non-activated position to a second, activated position causes said second end to move proximally within said housing;
  (iii) a driving member adapted to engage said second end of said driving arm, such that when the driving member and driving arm are engaged movement of said actuating member from said first, non-activated position to said second, activated position causes said driving member to move proximally from a default position to a release position, wherein said default position is proximal to said release position, wherein further said driving member is adapted to disengage said second end of said driving arm at said release position;
  (iv) a needle having a proximal portion and a distal portion positioned distally of said driving member, said needle retained within said housing at said proximal portion thereof, said needle further being slideable in a distal direction from a resting position to an extended position, wherein the extended position is distal to the resting position, wherein the needle has a closed distal tip;
  (v) a compression spring comprising a first portion in communication with said driving member and a second portion in communication with a fixed portion of said housing located proximally of said compression spring; wherein said compression spring is adapted to store potential energy when said driving member moves from said default position to said release position, said compression spring being adapted to return said driving member distally when said driving member disengages said second end of said driving arm, said driving member adapted to propel said needle in the distal direction to said extended position due to propulsion from said spring;
  (vi) a return spring, wherein the return spring is in communication with said actuating member, wherein said return spring is configured to automatically return said actuating member to said first, non-activated position after said driving arm disengages from said driving member, wherein the second end of said driving arm is configured to reengage said driving member as said actuating member returns to said first non-activated position; and
  (vii) a dampening element located in said housing distally of the proximal portion of said needle, wherein said dampening element is adapted to absorb the impact of said needle against said housing when said needle moves in the distal direction to said extended position and to return said needle to said resting position by urging the needle proximally to move the needle in a proximal direction, opposite to the distal direction and toward the housing, back to the resting position, such that the needle is moved distally and proximally by the urging of the compression spring and the dampening element, respectively.

15. The reciprocating needle biopsy device of claim 14, wherein said second end of said driving arm comprises a protrusion that releasably mates with a recess in an outer surface of said driving member.

16. The reciprocating needle biopsy device of claim 14, wherein said return spring returns said driving arm into engagement with said driving member when said driving member is returned to said default position.

17. The reciprocating needle biopsy device of claim 14, wherein said actuating member comprises a trigger button.

18. The reciprocating needle biopsy device of claim 14, wherein said driving member comprises stainless steel.

19. A reciprocating needle biopsy device, comprising:
  (i) a housing;
  (ii) a needle having a proximal portion and a distal portion and further comprising a lumen, said needle being slidably retained at said proximal portion thereof within said housing, said needle adapted to move longitudinally within said housing from a default position to a release position, wherein the release position is distal to the default position, wherein the needle has a closed distal tip at a distal end and is fixedly attached to a hub at a proximal end;
  (iii) a firing mechanism adapted to releasably engage said needle, said firing mechanism comprising a firing member configured to move said needle longitudinally in a distal direction from said default position to said release position, wherein the release position is distal to the default position, wherein further said firing mechanism further comprises a spring configured to return said needle to said default position by urging the needle proximally to move the needle in a proximal direction, opposite to the distal direction and toward the housing, back to the default position after the needle has been moved to the release position by the firing member, wherein the spring is engaged with the housing at a first end and engaged with the hub at a second end, wherein the spring is disposed distally of the hub;

(iv) an actuating member, wherein the actuating member is configured to actuate the firing mechanism; and (v) a cutter positioned within the lumen and adapted to advance distally within said lumen independently of said firing mechanism;

wherein actuation of the firing mechanism performs a sequential action of moving said needle distally from the default position to the release position, under the urging of said firing member, while storing potential energy in said spring immediately followed by disengagement from said needle enabling immediate return of said needle from the release position to the default position in the proximal direction, opposite to the distal direction and toward the housing, under the urging of said spring to complete a first reciprocating motion of said needle.

20. A method of penetrating dense tissue and obtaining a tissue sample comprising the steps of:

(i) providing a reciprocating needle biopsy device comprising (a) a housing comprising an actuating member, the actuating member being moveable from a first, non-activated position to a second, activated position, (b) a driving arm comprising a first end and a second end, wherein the first end is pivotally attached to the actuating member, such that movement of the actuating member from the first, non-activated position to a second, activated position causes the second end to move proximally within the housing, (c) a driving member adapted to engage the second end of the driving arm, such that when the driving member and driving arm are engaged movement of the actuating member from the first, non-activated position to the second, activated position causes the driving member to move proximally from a default position to a release position, wherein further the driving member is adapted to disengage the second end of the driving arm at the release position, (d) a needle having a proximal portion and a distal portion positioned distally of the driving member, the needle retained within the housing at the proximal portion thereof, the needle further being slideable in a distal direction from a resting position to an extended position, wherein the extended position is distal to the resting position, wherein the needle has a closed distal tip, (e) a compression spring comprising a first portion in communication with the driving member and a second portion in communication with a fixed portion of the housing located proximally of the compression spring; wherein the compression spring is adapted to store potential energy when the driving member moves from the default position to the release position, the compression spring being adapted to return the driving member distally when the driving member disengages the second end of the driving arm, the driving member adapted to propel the needle in the distal direction to the extended position due to propulsion from the spring, (f) a return spring, wherein the return spring is in communication with the actuating member, wherein the return spring is configured to automatically return the actuating member to the first, non-activated position after the driving arm disengages from the driving member, wherein the second end of the driving arm is configured to reengage the driving member as the actuating member returns to the first non-activated position, and (g) a dampening element located in the housing distally of the proximal portion of the needle, wherein the dampening element is adapted to absorb the impact of the needle against the housing when the needle moves in the distal direction to the extended position and to return the needle to the resting position by urging the needle proximally to move the needle in a proximal direction, opposite to the distal direction and toward the housing, back to the resting position, such that the needle is moved distally and proximally by the urging of the compression spring and the dampening element, respectively, (h) a cutter positioned within the needle adapted to advance distally within the needle independently of actuation of the reciprocating needle biopsy device;

(ii) inserting the reciprocating needle biopsy device into tissue, wherein a portion of the tissue comprises tissue of interest;

(iii) actuating a reciprocating firing stroke of the reciprocating needle biopsy device while the distal portion of the needle is in the tissue by transitioning the actuating member from the first, non-activated position to the second, activated position, thereby causing the distal portion of the needle to sequentially extend distally from the resting position to the extended position and immediately retract proximally from the extended position to the resting position such that the distal portion of the needle remains within the tissue during the entire firing stroke, wherein the actuating member automatically returns to the first, non-activated position from the second, activated position during the firing stroke;

(iv) repeating step (iii) as necessary to place the reciprocating needle biopsy device adjacent to the tissue of interest:

(v) placing the reciprocating needle biopsy device adjacent to the tissue of interest;

(vi) advancing the cutter through the needle independently of actuation of the needle biopsy device; and (vii) obtaining a sample of the tissue of interest after the reciprocating needle biopsy device has been placed adjacent the tissue of interest.

* * * * *